United States Patent
Yeung et al.

(10) Patent No.: US 8,361,007 B2
(45) Date of Patent: Jan. 29, 2013

(54) U-SHAPED DISC SHUNT AND DELIVERY DEVICE

(75) Inventors: Jeffrey E. Yeung, San Jose, CA (US); Teresa T. Yeung, San Jose, CA (US)

(73) Assignee: Aleeva Medical Inc., San Jose, CA (US)

( * ) Notice: Subject to any disclaimer, the term of this patent is extended or adjusted under 35 U.S.C. 154(b) by 793 days.

(21) Appl. No.: 12/223,370

(22) PCT Filed: Feb. 5, 2007

(86) PCT No.: PCT/US2007/003194
§ 371 (c)(1), (2), (4) Date: Jul. 29, 2008

(87) PCT Pub. No.: WO2007/089947
PCT Pub. Date: Aug. 9, 2007

(65) Prior Publication Data
US 2009/0024071 A1    Jan. 22, 2009

Related U.S. Application Data

(60) Provisional application No. 60/765,147, filed on Feb. 4, 2006, provisional application No. 60/784,631, filed on Mar. 22, 2006, provisional application No. 60/788,936, filed on Apr. 4, 2006.

(51) Int. Cl.
*A61M 5/00* (2006.01)
*A61M 25/00* (2006.01)
(52) U.S. Cl. .......................................... 604/8; 604/264
(58) Field of Classification Search ............... 604/8, 264
See application file for complete search history.

(56) References Cited

U.S. PATENT DOCUMENTS

| | | | | |
|---|---|---|---|---|
| 2,734,507 A * | 2/1956 | Nichols | .......................... | 606/231 |
| 3,424,164 A * | 1/1969 | Messores et al. | ............. | 606/228 |
| 5,061,274 A * | 10/1991 | Kensey | .......................... | 606/213 |
| 6,110,155 A * | 8/2000 | Baudino | ........................ | 604/265 |
| 6,562,033 B2 * | 5/2003 | Shah et al. | ...................... | 606/41 |
| 2003/0199844 A1 * | 10/2003 | LaVon et al. | ............. | 604/385.14 |
| 2004/0210209 A1 * | 10/2004 | Yeung et al. | .................. | 604/500 |

* cited by examiner

*Primary Examiner* — Susan Su
(74) *Attorney, Agent, or Firm* — Carol Titus GSS Law Group

(57) ABSTRACT

The intervertebral disc contains no blood vessels. Nutrients and waste are diffused mainly through adjacent vertebral bodies. As we age, calcified layers form between the disc and vertebral bodies, blocking diffusion. The disc begins to starve and flatten. The weight shifts abnormally from disc to the facet joints causing strain and back pain. Under anaerobic conditions, lactic acid is produced causing acidic irritation and unspecific pain. A U-shaped disc shunt (126) is delivered into and sealed within the degenerated disc simply by needle puncturing and withdrawal, to draw nutrients from bodily circulation into the avascular disc. A continual supply of nutrients increases biosynthesis of the water-retaining sulfated glycosaminoglycans, hence swelling pressure within the disc. The weight is re-shifted from the facet joints to the regenerated disc, alleviating back pain. With oxygen transported through the shunt, anaerobic production of lactic acid is minimized. In addition, the residual lactic acid is expelled through the U-shaped shunt during disc compression into bodily circulation to alleviate unspecific pain.

41 Claims, 18 Drawing Sheets

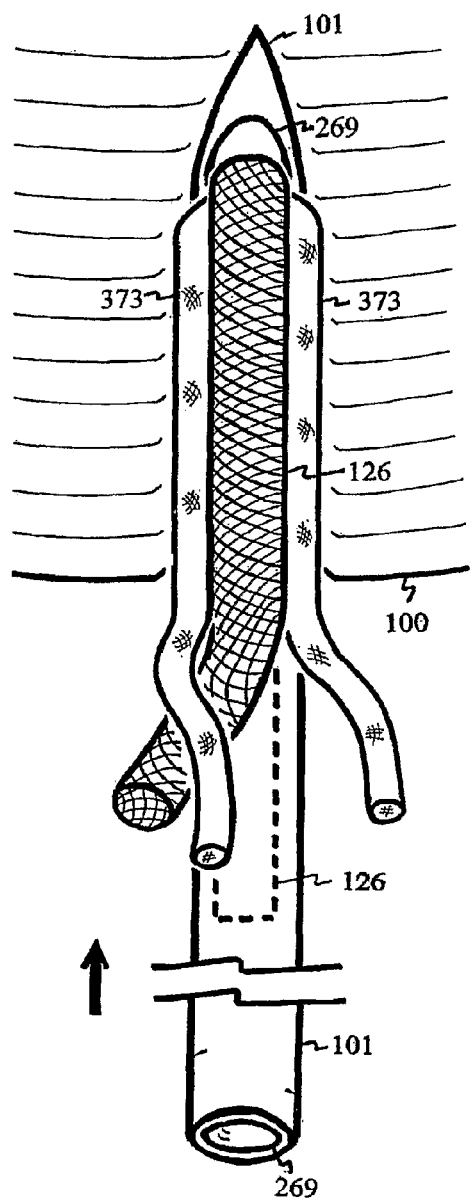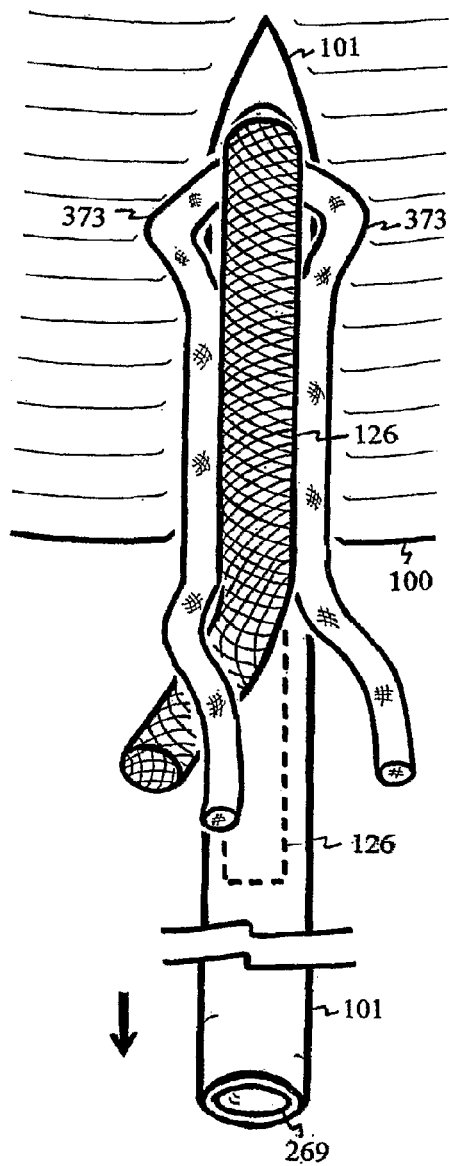
Figure 13
Figure 14

U-SHAPED DISC SHUNT AND DELIVERY DEVICE

CROSS-REFERENCE TO OTHER APPLICATIONS

This application is a National Stage Application of PCT/US07/03194 filed Feb. 5, 2007, which claimed priority of U.S. Provisional Applications 60/765,147 filed on Feb. 4, 2006; 60/784,631 filed on Mar. 22, 2006; and 60/788,936 filed on Apr. 4, 2006.

FIELD OF INVENTION

The disc shunt is used to re-establish the exchange of nutrients and waste between the avascular disc and bodily circulation to alleviate back pain. This invention relates to a U-shaped disc shunt and delivery device to preserve hydrostatic disc pressure, simplify delivery and increase permeability of nutrients into the avascular disc.

BACKGROUND

Low back pain is a leading cause of disability and lost productivity. Up to 90% of adults experience back pain at some time during their lives. For frequency of physician visits, back pain is second only to upper respiratory infections. In the United States, this malady disables 5.2 million people, and the economic impact has been reported to be as high as $100 billion each year. Though the sources of low back pain are varied, in most cases the intervertebral disc is thought to play a central role. Degeneration of the disc initiates pain in other tissues by altering spinal mechanics and producing non-physiologic stress in surrounding tissues.

The intervertebral disc absorbs most of the compressive load of the spine, but the facet joints of the vertebral bodies share approximately 16%. The disc consists of three distinct parts: the nucleus pulposus, the annular layers and the cartilaginous endplates. The disc maintains its structural properties largely through its ability to attract and retain water. A normal disc contains 80% water in the nucleus pulposus. The nucleus pulposus within a normal disc is rich in water absorbing sulfated glycosaminoglycans (chondroitin and keratan sulfate), creating the swelling pressure to provide tensile stress within the collagen fibers of the annulus. The swelling pressure produced by high water content is crucial to supporting the annular layers for sustaining compressive loads.

In adults, the intervertebral disc is avascular. Survival of the disc cells depends on diffusion of nutrients from external blood vessels and capillaries through the cartilage of the endplates. Diffusion of nutrients also permeates from peripheral blood vessels adjacent to the outer annulus, but these nutrients can only permeate up to 1 cm into the annular layers of the disc. An adult disc can be as large as 5 cm in diameter; hence diffusion through the cranial and caudal endplates is crucial for maintaining the health of the nucleus pulposus and inner annular layers of the disc.

Calcium pyrophosphate and hydroxyapatite are commonly found in the endplate and nucleus pulposus. Beginning as young as 18 years of age, calcified layers begin to accumulate in the cartilaginous endplate. The blood vessels and capillaries at the bone-cartilage interface are gradually occluded by the build-up of the calcified layers, which form into bone. Bone formation at the endplate increases with age.

When the endplate is obliterated by bone, diffusion of nutrients through the calcified endplate is greatly limited. In addition to hindering the diffusion of nutrients, calcified endplates further limit the permeation of oxygen into the disc. Oxygen concentration at the central part of the nucleus is extremely low. Cellularity of the disc is already low compared to most tissues. To obtain necessary nutrients and oxygen, cell activity is restricted to being on or in very close proximity to the cartilaginous endplate. Furthermore, oxygen concentrations are very sensitive to changes in cell density or consumption rate per cell.

The supply of sulfate into the nucleus pulposus for biosynthesizing sulfated glycosaminoglycans is also restricted by the calcified endplates. As a result, the sulfated glycosaminoglycan concentration decreases, leading to lower water content and swelling pressure within the nucleus pulposus. During normal daily compressive loading on the spine, the reduced pressure within the nucleus pulposus can no longer distribute forces evenly along the circumference of the inner annulus to keep the lamellae bulging outward. As a result, the inner lamellae sag inward while the outer annulus continues to bulge outward, causing delamination of the annular layers.

The shear stresses causing annular delamination and bulging are highest at the posteriolateral portions adjacent to the neuroforamen. The nerve is confined within the neuroforamen between the disc and the facet joint. Hence, the nerve at the neuroforamen is vulnerable to impingement by the bulging disc or bone spurs.

When oxygen concentration in the disc falls below 0.25 kPa (1.9 mmHg), production of lactic acid dramatically increases with increasing distance from the endplate. The pH within the disc falls as lactic acid concentration increases. Lactic acid diffuses through micro-tears of the annulus irritating the richly innervated posterior longitudinal ligament, facet joint and/or nerve root. Studies indicate that lumbar pain correlates well with high lactate levels and low pH. The mean pH of symptomatic discs was significantly lower than the mean pH of normal discs. Acid concentration is three times higher in symptomatic discs than normal discs. In symptomatic discs with pH 6.65, the acid concentration within the disc is 5.6 times the plasma level. In some preoperative symptomatic discs, nerve roots were found to be surrounded by dense fibrous scars and adhesions with remarkably low pH 5.7-6.30. The acid concentration within these discs was 50 times the plasma level.

Approximately 85% of patients with low back pain cannot be given a precise pathoanatomical diagnosis. This type of pain is generally classified under "non-specific pain". Back pain and sciatica can be recapitulated by maneuvers that do not affect the nerve root, such as intradiscal saline injection, discography, and compression of the posterior longitudinal ligaments. It is possible that some of the non-specific pain is caused by lactic acid irritation secreted from the disc. Injection into the disc can flush out the lactic acid. Maneuvering and compression can also drive out the irritating acid to produce non-specific pain. Currently, no intervention other than discectomy can halt the production of lactic acid.

In the presence of oxygen, metabolism of each glucose molecule produces 36 adenosine triphosphates, ATP, through glycolysis, citric acid cycle and electron transport chain. ATP is a high-energy compound essential for driving biosynthesis of the water-retaining proteoglycans. Under anaerobic conditions, the metabolism of each glucose molecule produces only 2 ATP and two lactic acids. Hence, production of high-energy compound ATP is low under anaerobic conditions within the disc.

The nucleus pulposus is thought to function as "the air in a tire" to pressurize the disc. To support the load, the pressure effectively distributes the forces evenly along the circumference of the inner annulus and keeps the lamellae bulging outward. The process of disc degeneration begins with calcification of the endplates, which hinders diffusion of sulfate and oxygen into the nucleus pulposus. As a result, production of the water absorbing sulfated glycosaminoglycans is significantly reduced, and the water content within the nucleus decreases. The inner annular lamellae begin to sag inward, and the tension on collagen fibers within the annulus is lost. The degenerated disc exhibits unstable movement, similar to a flat tire. Approximately 20-30% of low-back-pain patients have been diagnosed as having spinal segmental instability. The pain may originate from stress and increased load on the facet joints and/or surrounding ligaments. In addition, pH within the disc becomes acidic from the anaerobic production of lactic acid, which irritates adjacent nerves and tissues.

The method of endplate puncturing for drawing nutrients from the vertebral body to regenerate the degenerated disc is described in PCT/US2002/04301 (WO 2002/064044) by J. Yeung and T. Yeung filed on Feb. 13, 2002 with US Provisional application 60/268666 filed on Feb. 13, 2001.

Shunts or conduits for re-establishing the exchange of nutrients and waste between the degenerative disc and bodily circulation is described in PCT/US2004/14368 (WO 2004/101015) and U.S. application Ser. Nos. 10/840,816 by J. Yeung and T. Yeung, both applications filed on May 7, 2004. U.S. provisional patent application 60/626,644, filed on Nov. 10, 2004 by Jeffrey E. Yeung also described several disc shunt (conduit) configurations and delivery devices.

Discs L4-5 and L5-S1 are shielded by the iliac, inaccessible by straight needle from outside to deliver the conduit into the disc. However, through the pedicle of the vertebral body, the elastically curved needle proposed in PCT/US2005/22749 (WO 2006/002417), filed on Jun. 22, 2005 by J. Yeung, can puncture through the calcified endplate to deliver the shunt or conduit for exchanging nutrients and lactate between the avascular disc and bodily circulation.

Chemical or physical modification of the disc shunt was proposed in PCT/US2006/44795, filed on Nov. 17, 2006 by James E. Kemler and Jeffrey E. Yeung for enhancing, selecting or delaying molecular transport into and out of the avascular disc.

By re-supplying the disc cells with nutrients and oxygen through disc shunt or conduit, biosynthesis of sulfated glycosaminoglycans may increase to retain additional water and sustain compressive loading. Hence, segmental instability and excessive loading of facet joints are minimized to alleviate back pain. With the presence of additional oxygen, production of lactic acid may decrease to minimize acidic irritation and increase production of ATP, driving biosynthesis of the water-retaining proteoglycans.

SUMMARY OF INVENTION

One end of a U-shaped shunt is inserted into the lumen of a needle while the other end is draped outside the needle. As the needle punctures into a disc, the outside strand of the shunt is squeezed beside the outside wall of the needle, pressing into the annulus through a very small punctured hole. During needle withdrawal, the friction between the outside strand and the annulus grips the U-shaped shunt, allowing the inside strand to slide out the lumen of the needle to deploy the U-shaped shunt within the disc. Since the U-shaped shunt is tightly press-fitted into the elastic annulus, hydrostatic pressure is preserved within the shunted disc.

Another U-shaped shunt can be linked to the outside strand to increase (1) friction for shunt deployment, (2) press-fit capacity, and (3) rate of nutrient and waste exchange to regenerate the intervertebral disc. Additives, buffer, nutrients, growth factor and cells can also be incorporated into the U-shaped shunts to expedite disc regeneration and alleviate back pain.

REFERENCE NUMBER

100 Intervertebral disc
101 Needle
103 Trocar
105 Endplate
108 Calcified layer or blockade
114 Annular delamination
126 U-shaped disc shunt or conduit
128 Nucleus pulposus
129 Facet joint
150 Drill
159 Vertebral body
230 Sleeve needle
269 Lumen of needle
278 Pedicle
279 Drill stop or step
360 Stem
362 Indentation of the stem
363 Bevel of the stem
364 Body of the stem
366 Edge of the stem
367 Restriction device
368 Sharp inner wall of needle
369 Damage portion of the shunt
370 Dull, round or blunt inner wall of the needle
371 Slit of the needle
372 Protrusion or anchor of U-shaped shunt
373 Link or attached shunt
403 Prong

DESCRIPTION OF THE DRAWINGS

FIG. 13 shows the needle 101, shunt 126 and link shunt 373 puncturing and press-fitting into the annular layers to preserve hydrostatic pressure of the disc 100.

FIG. 14 depicts spreading or kinking of the link shunt 373 to add friction between the link shunt 373 and annulus during withdrawal of the needle 101.

DETAILED DESCRIPTION OF THE EMBODIMENTS

Figure 1:
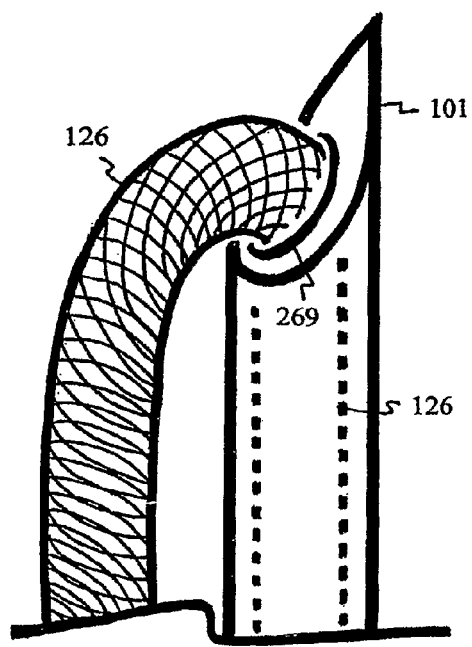
FIG. 1 shows a portion of disc shunt 126 extending from the lumen 269 and draping over the outside wall of a needle 101.

Disc shunt 126 is a flexible and semi-permeable conduit transporting nutrients, waste and oxygen between bodily circulation and the avascular disc 100. The disc shunt 126 is bent into a U- or V-configuration. The U- or V-portion is the middle portion of the disc shunt 126, which is distal to a first end and a second end of the disc shunt 126. The lengths of the bent portions do not have to be equal. One end of the U-shaped shunt 126 is inserted into the lumen 269 of a thin needle 101 while the other end of the U-shaped shunt 126 is draped over the outside wall of the thin needle 101, as shown in FIG. 1.

Figure 2:
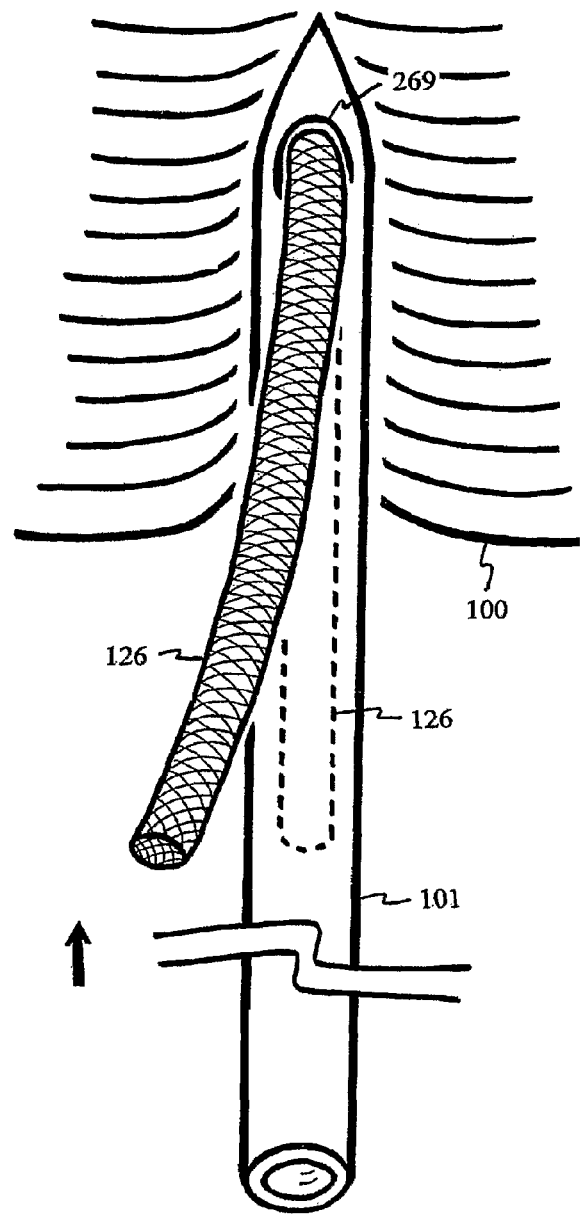
FIG. 2 depicts needle 101 puncturing to press-fit the shunt 126 into annular layers of the intervertebral disc 100 to preserve hydrostatic disc pressure.
Figure 3:
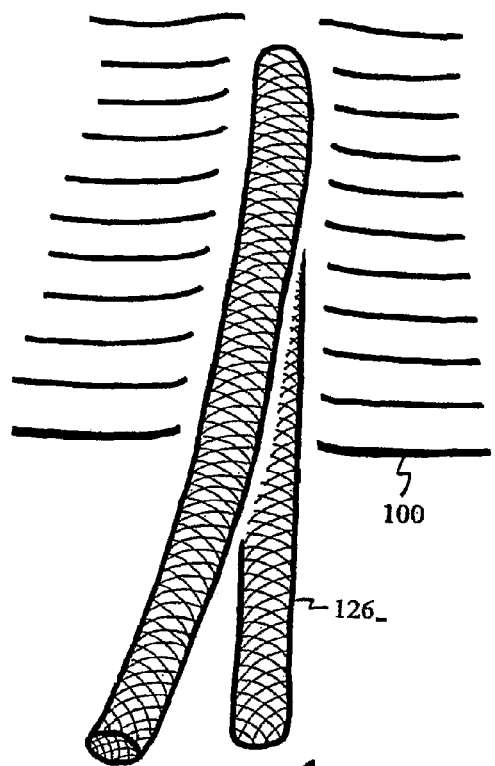
FIG. 3 shows withdrawal of the needle 101 to deploy the shunt 126 within and extending from the disc 100.
Figure 3:
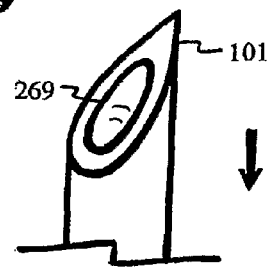

Since diffusion of nutrients can only penetrate up to 1 cm into the annular layers, the U-shaped disc shunt 126 is delivered deep into the annulus by puncturing the disc 100 with the needle 101, as shown in FIG. 2. As the needle 101 punctures into the disc 100, the outside strand of the U-shaped shunt 126 is pulled, dragged and tightly pressed against the annular layers beside the outside wall of the needle 101 through a small puncture hole. During needle 101 withdrawal, the contact friction between the annulus and the outside strand of the U-shaped shunt 126 holds or anchors the shunt 126, allowing the inside strand to slide out the lumen 269 of the needle 101, as shown in FIG. 3. Since one strand is press-fitted within a small puncture, the U-shaped shunt 126 is well sealed within the elastic annular layers to preserve the hydrostatic pressure of the disc 100.

FIG. 3 shows that the U-loop of the shunt 126 is deployed within the disc 100 with the proximal ends of the shunt 126 extending outside the disc 100, in contact with bodily circulation. As a result, the exchange of nutrients, oxygen and lactic acid between the avascular disc 100 and bodily circulation is re-established to (1) increase biosynthesis of the water-retaining sulfated glycosaminoglycans and swelling pressure for sustaining disc compression, (2) decrease strain on the facet joints and pain from segmental instability, (3) lower production of the irritating lactic acid by converting anaerobic to aerobic metabolism, (4) increase production of ATP through the aerobic metabolism pathway to energize disc 100 regeneration, and (5) expel lactic acid through the shunt 126 to minimize irritation. In essence, the U-shaped disc shunt 126 is deployed to halt disc 100 degeneration and alleviate back pain.

One leg, portion or end of the U-shaped shunt 126 occupies the lumen 269 inside the needle 101 while the other leg, portion or end hangs outside the needle 101. The inside portion of the shunt 126 is free to exit the lumen 269 of the needle 101. The wall of the needle 101 at the distal end provides support to the U-loop of the shunt 126 for disc 100 puncturing. In addition to providing friction for shunt 126 deployment, the outside portion of the shunt 126 is pressed or squeezed beside or along the needle 101 wall as it enters the annulus. Hence, the U-shaped shunt 126 is delivered through a very small needle puncture hole. After needle 101 withdrawal, the elastic annular layers seal around the deployed and press-fitted shunt 126 to preserve the hydrostatic pressure of the disc 100.

Figure 4:
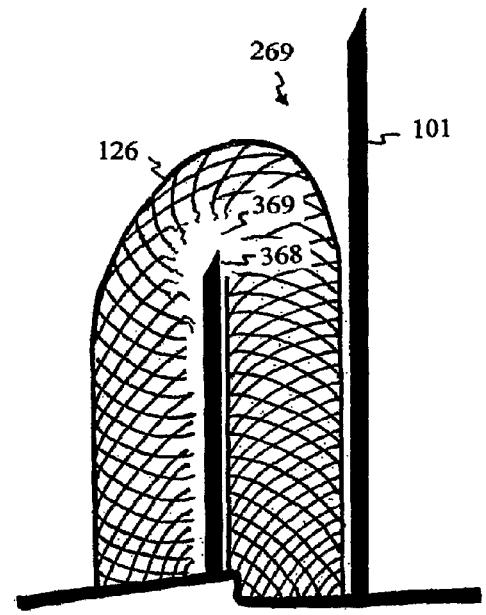
FIG. 4 depicts a longitudinal view of the shunt 126 with a damaged portion 369 cut by the sharp inner wall 368 of the needle 101 during disc 100 puncturing.

The sharp distal end of the needle 101 usually contains a sharp knife-like edge 368 formed by the inner wall of the beveled lumen 269, as shown in FIG. 4. When the disc 100 is punctured during implantation of the press-fitting U-shaped shunt 126, the knife-like edge of the inner wall 368 inevitably shears and damages the U-loop of the shunt 126. The damaged portion 369 of the shunt 126 forms small fibers or shedding debris, which causes significant tissue reaction to the otherwise inert material. During in-vitro studies, shearing was so serious that many U-shaped shunts 126 were severed at the U-loops during press-fit disc 100 puncturing. As a result, the inside portion of the shunt 126 remained within the lumen 269 of the withdrawn needle 101. With only one strand of the U, the shunt 126 was no longer press-fitting into the intervertebral disc 100, so it decreased its ability to preserve the hydrostatic pressure of the disc 100.

Figure 5:
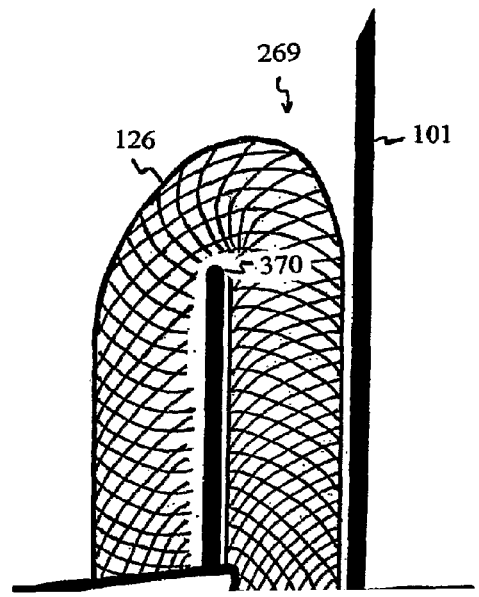
FIG. 5 shows a rounded or blunt inner wall 370 at the lumen 269 opening to prevent shearing or damaging the shunt 126 during disc 100 puncturing.

FIG. 5 shows a rounded or blunt inner wall 370 at the beveled lumen 269 of a needle 101. The rounded or blunt inner wall 370 can be formed by machining to prevent damage to the shunt 126 during press-fit disc 100 puncturing, as shown in FIG. 5. It is also possible to pad, cover, coat or fortify the U-loop of the U-shaped shunt 126 to minimize damage by the sharp inner wall 368 of the needle 101. In addition, the U-loop can be made with a shear-proof material to avoid damage during press-fit puncturing.

Figure 6:
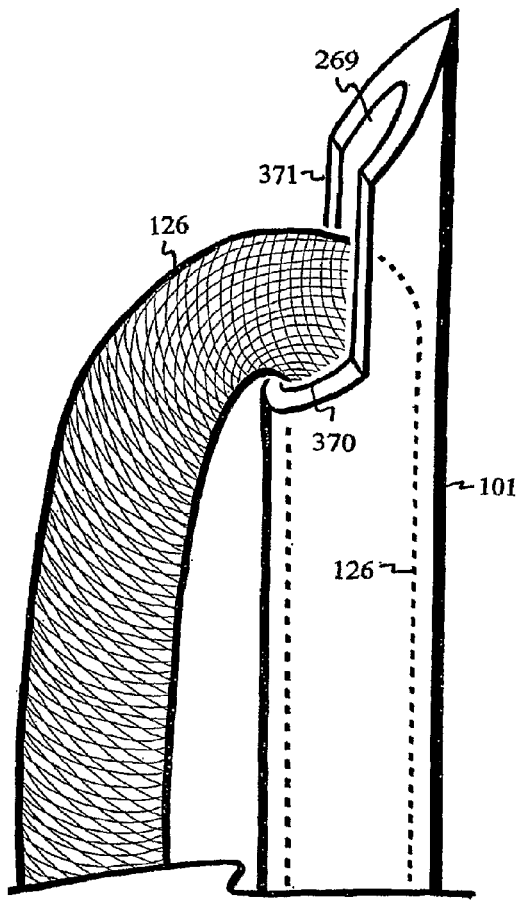
FIG. 6 shows a slit 371 opened from the lumen 269, forming a step or indentation to shield the shunt 126 from shearing during disc 100 puncturing.

FIG. 6 shows a slit 371 opened into the lumen 269 placing the U-loop of the shunt 126 further away from the sharp tip of the needle 101. The additional separation between the sharp tip and the U-loop facilitates disc 100 puncture by setting up sequential press-fit positions to gradually enlarge the puncture site. The needle 101 tip spearheads the entry followed by the U-loop into the annular layers of the intervertebral disc 100. In addition, gradual enlargement of the puncture site may minimize shearing or damage to the U-shaped shunt 126 during disc 100 puncture. Entrenching or shielding the U-loop in the slit 371 may further protect the shunt 126 from shearing during press-fit entry into the disc 100. In addition, the sharp knife-like edge 368 formed by inner wall of the indented lumen 269 of the needle 101 can also be rounded or made blunt to further prevent damage to the U-shaped shunt 126.

Figure 7:
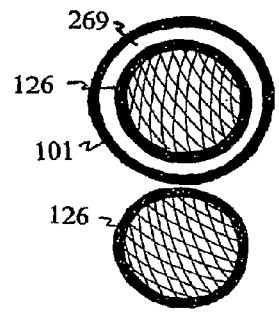
FIG. 7 shows a cross section of the disc shunt 126, inside and outside the needle 101. Deployment of disc shunt 126 depends primary on the friction between the annulus and the section of disc shunt 126 outside the needle 101.
Figure 8:
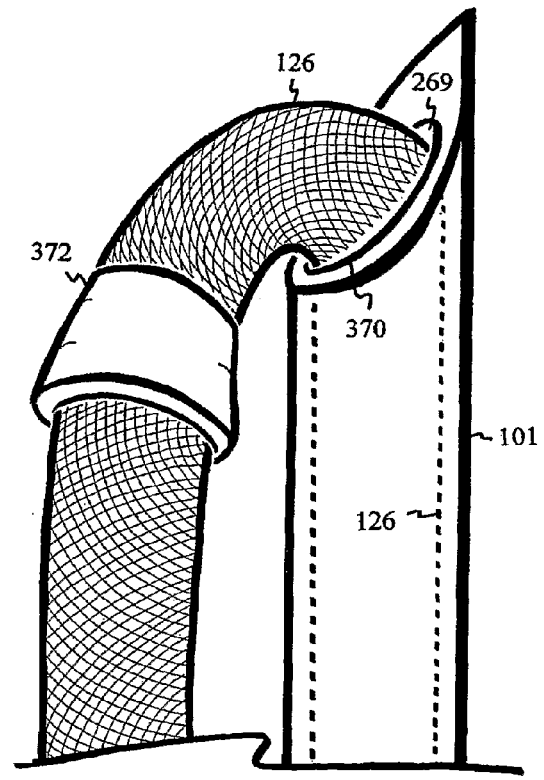
FIG. 8 shows an anchor or tapered protrusion 372 on the outside portion of the shunt 126 to add friction and assist shunt 126 deployment during withdrawal of the needle 101.
Figure 10:
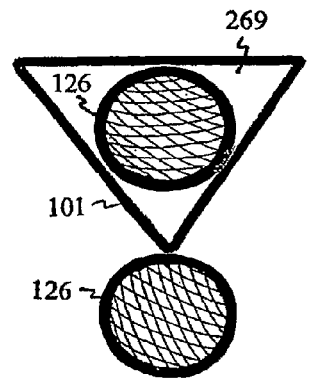
FIG. 10 shows a cross section of the triangular needle 101 and disc shunt 126 extending from the lumen 269 and draping over a vertex of the triangle to minimize friction between the shunt 126 and needle 101.
Figure 12:
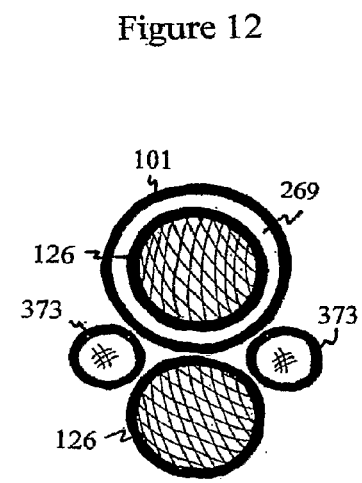
FIG. 12 shows a cross section of the needle 101, shunt 126 and link shunt 373 to increase transport of nutrients into the avascular disc and friction essential for shunt deployment.

Deployment of the U-shaped shunt 126 is driven by the friction between the annulus and the outside portion of the shunt 126. FIG. 7 shows a cross section of the inside and outside portions of the lumenless shunt 126 relative to the needle 101. Similar cross sections of the lumenless shunts 126 are shown in FIG. 10 and FIG. 12. The friction between the annulus and the outside portion of the shunt 126 can increase significantly by attaching an anchor or tapered protrusion 372 on the outside portion of the shunt 126, as shown in FIG. 8. The tapered protrusion 372 functions as a barb, allowing entry but preventing shunt 126 pull out from the disc 100.

Figure 9:
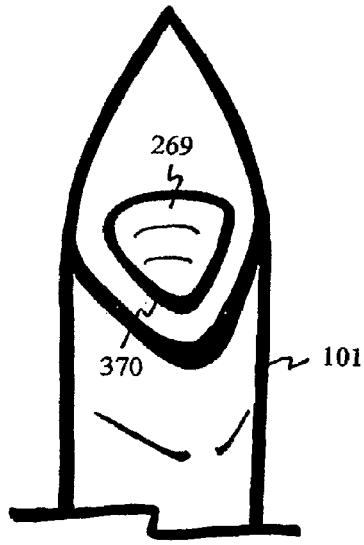
FIG. 9 shows a needle 101 with a triangular cross section. The needle 101 is sharpened, beveling to one side of the triangle.

Deployment of the U-shaped shunt 126 also depends on the friction between the outside portion of the shunt 126 and outside wall of the needle 101. FIG. 9 shows a needle 101 with a triangular cross section. The triangular needle 101 is sharpened to bevel toward one vertex of the triangle. The outside strand of U-shape shunt 126 is aligned with the outside edge of this vertex of the triangular needle 101. FIG. 10 shows a cross section of the triangular needle 101 and the U-shaped shunt 126 extending from the lumen 269 and draping over the triangular vertex to minimize contact surface and friction between the shunt 126 and needle 101. The needle 101 with a round or non-round cross section can also be lubricated inside and outside to decrease friction between the needle 101 and the shunt 126 for facilitating shunt 126 deployment during withdrawal of the needle 101. In addition, the outside portion of the shunt 126 can be coated with adhesive, swelling agent or crosslinking agent for disc 100 anchoring prior to needle 101 withdrawal.

Figure 11:
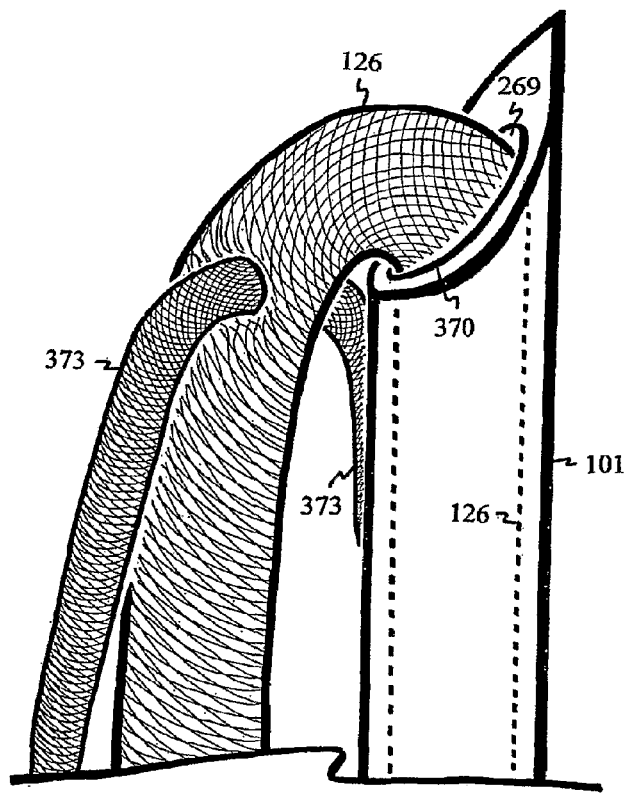
FIG. 11 shows a link shunt 373 threaded through or connected to the portion of disc shunt 126 outside the needle 101.

FIG. 11 shows a link shunt 373 threaded through or attached to the outside portion of the U-shaped shunt 126. The combination of U-shaped shunt 126 and link shunt 373 increases mass to (1) allow rapid exchange of nutrients and waste between the degenerative disc 100 and bodily circulation, (2) seal and preserve hydrostatic disc 100 pressure, and/or (3) anchor within the disc 100 for deployment during needle 101 withdrawal. FIG. 12 shows a cross section of the needle 101, shunt 126 and link shunt 373. The linked shunt 373 can differ from the U-shaped shunt 126 by having different (1) material, (2) pore size, (3) coating, (4) additives, (5) configuration, (6) diameter, (7) length, (8) shape, (9) texture, and/or (10) degradation profile.

FIG. 13 shows the needle 101 delivering the shunt 126 and link shunt 373 to press-fit into the annular layers and preserve hydrostatic pressure of the disc 100. The link shunt 373 can attach anywhere along the outside portion of the shunt 126. To position the sequential press-fit, attachment of the link shunt 373 should be slightly behind or away from the U-loop of the shunt to ease disc 100 puncture. In addition to aiding shunt 126 deployment, the link shunt 373 provides additional sealing capacity within the annulus to preserve hydrostatic pressure of the repaired disc 100.

Figure 15:
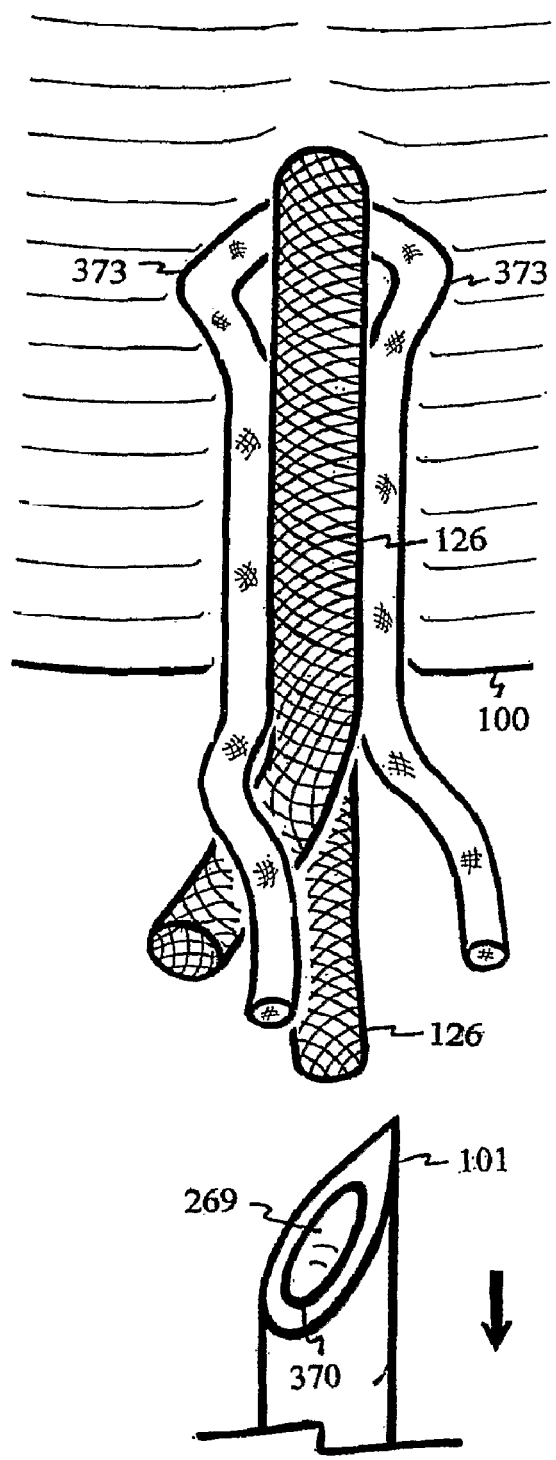
FIG. 15 shows deployment of the shunt 126 and link shunt 373 by withdrawing the needle 101 to re-establish the exchange of nutrients and waste between the avascular disc 100 and bodily circulation.

The link shunt 126 is likely to shift, buckle, kink and/or spread to add friction to the disc 100 during needle 101 withdrawal, as shown in FIG. 14. Similar movement and friction may apply to the outside portion of the U-shaped shunt 126. As a result, the inside portion of the shunt 126 slides and exits from the lumen 269 of the withdrawn needle 101, deploying both the linked shunts 126, 373 as shown in FIG. 15, to re-establish the exchange of nutrients and waste between the avascular disc 100 and surrounding circulation.

Figure 16:
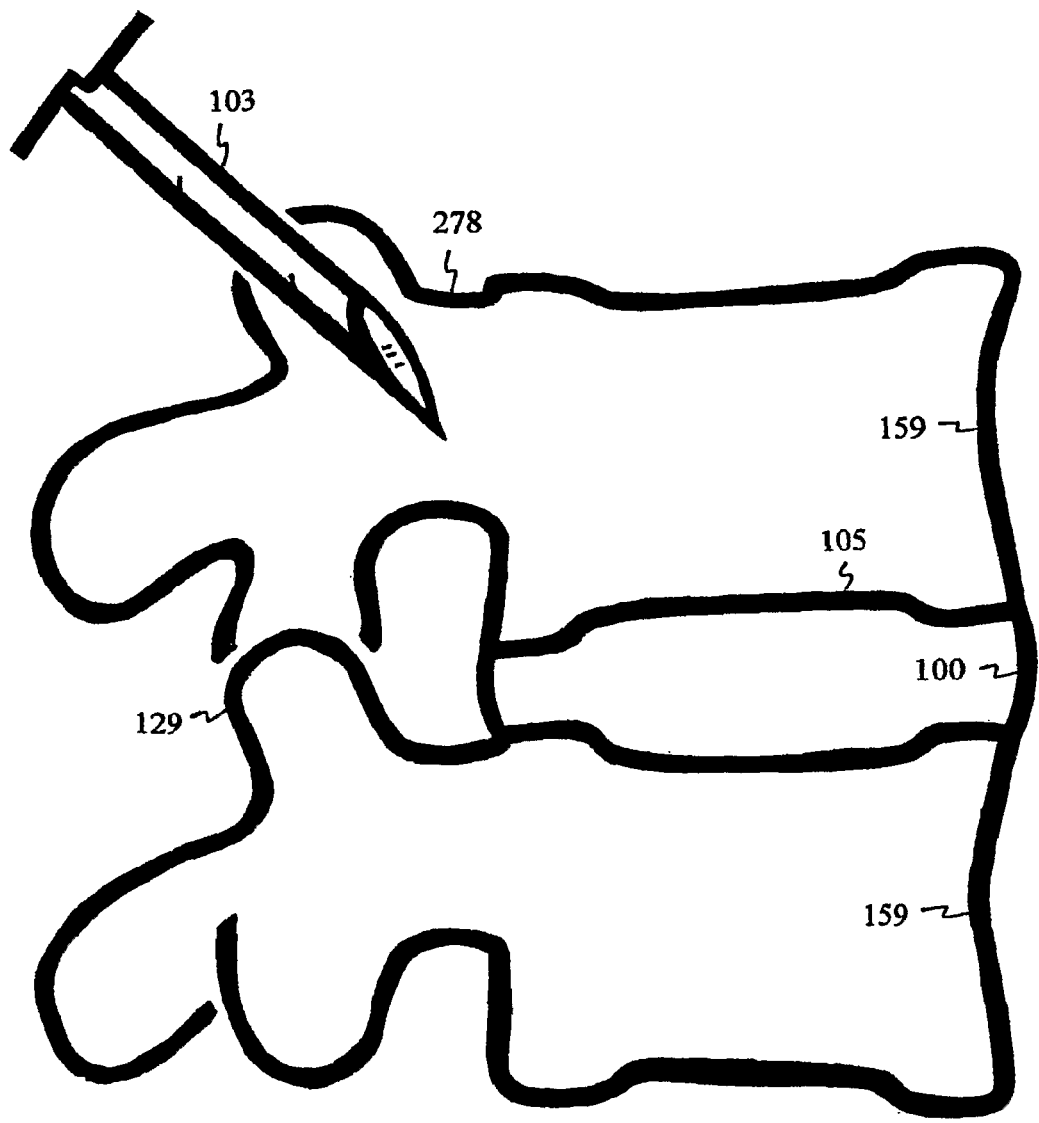
FIG. 16 shows a guided trocar 103 puncturing through soft tissue into the pedicle 278.
Figure 17:
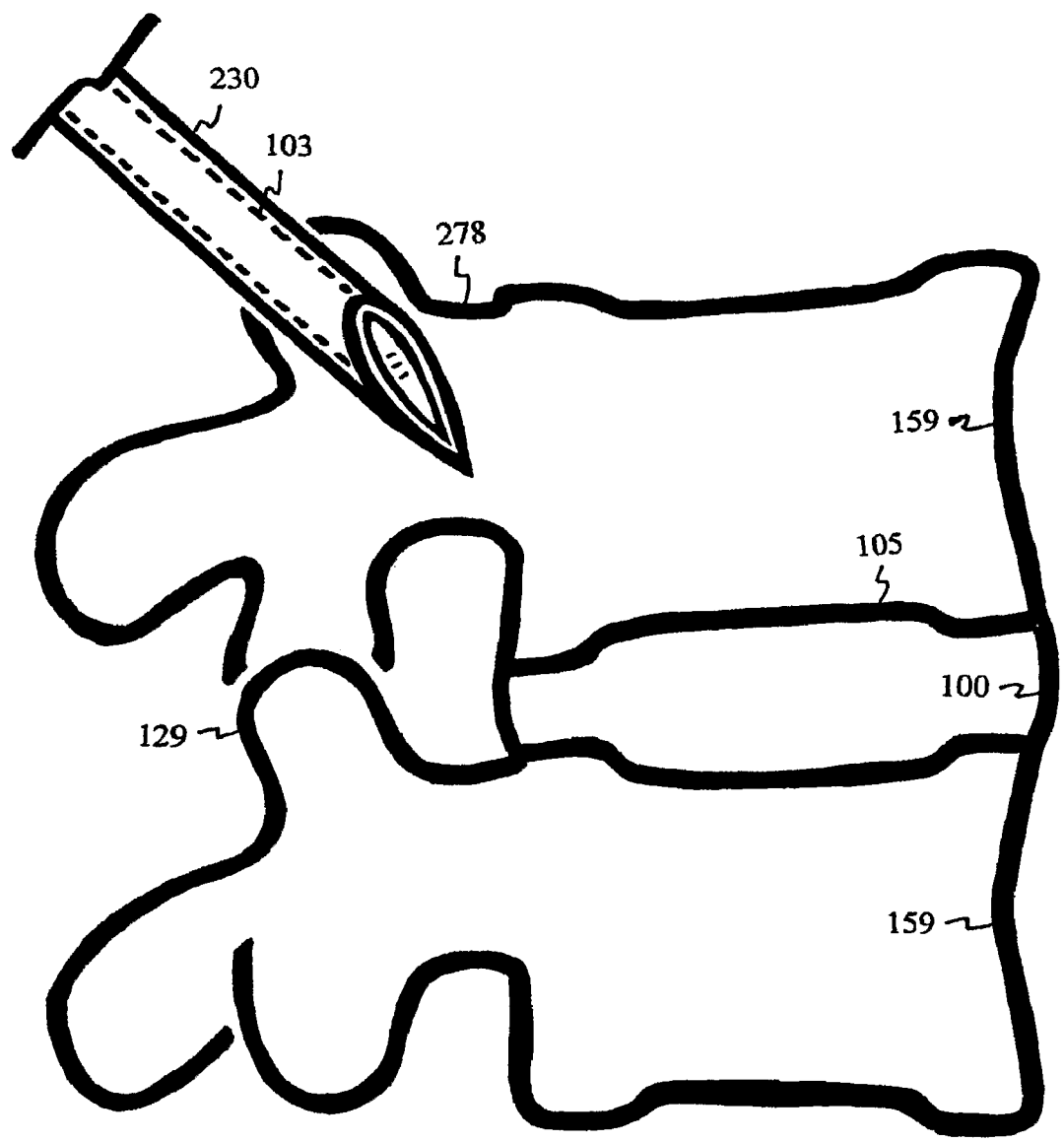
FIG. 17 shows a sleeve needle 230 inserted over the trocar 103 into the pedicle 278.

FIG. 16 shows a trocar 103, guided by fluoroscopes, puncturing soft tissue into the pedicle 278. The trocar 103 can be coated with radiopaque, echogenic or MRI visible coating to assist guidance and enhance imaging. FIG. 17 shows a sleeve needle 230 inserted over the trocar 103 sliding into the pedicle 278. The sleeve needle 230 can also be coated with radiopaque, echogenic, MRI coating or other coating for image enhancement.

Figure 18:
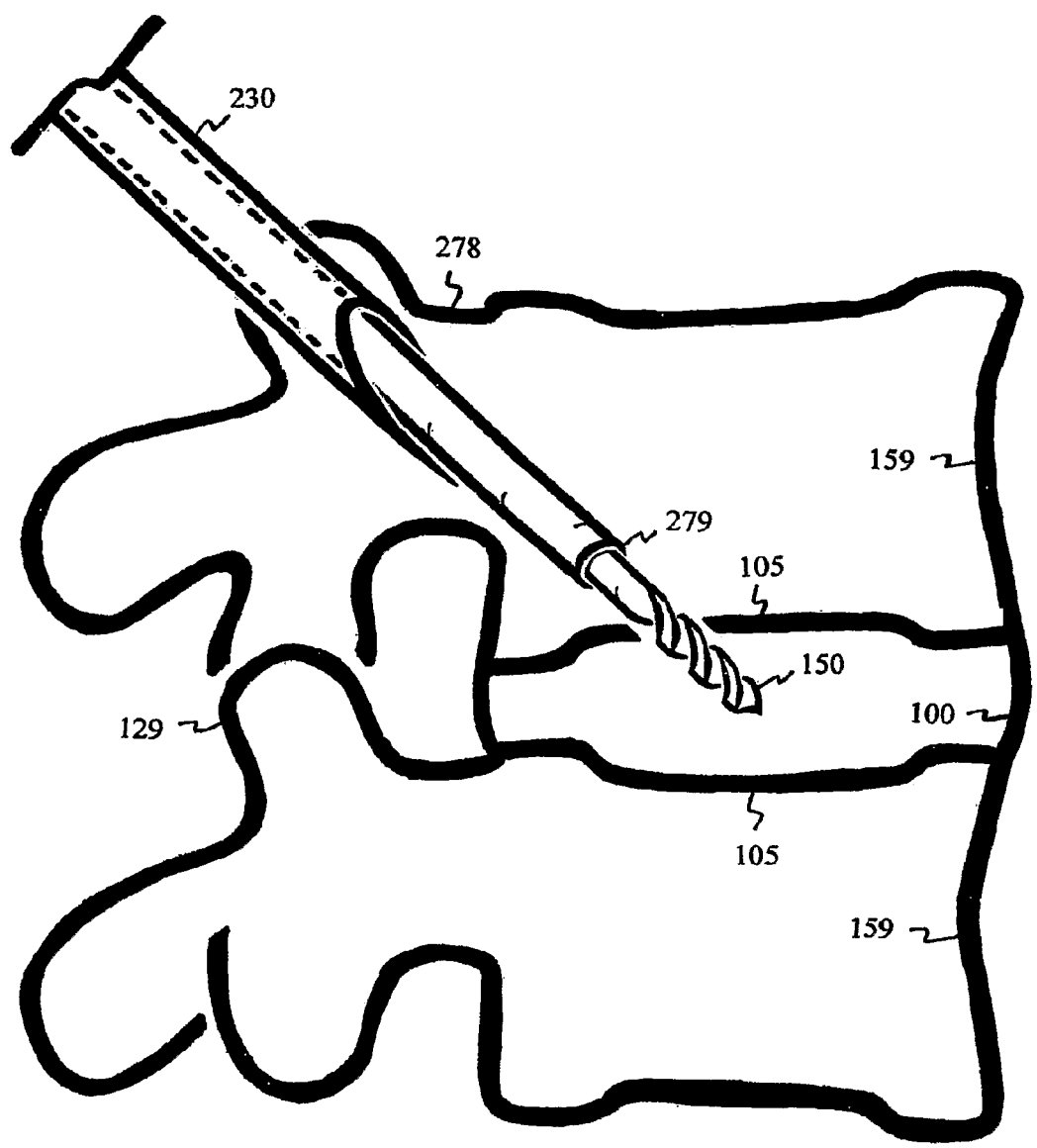
FIG. 18 shows replacement of the trocar 103 with a drill 150 in the sleeve needle 230, drilling through the calcified endplate 105 into the degenerated disc 100.
Figure 19:
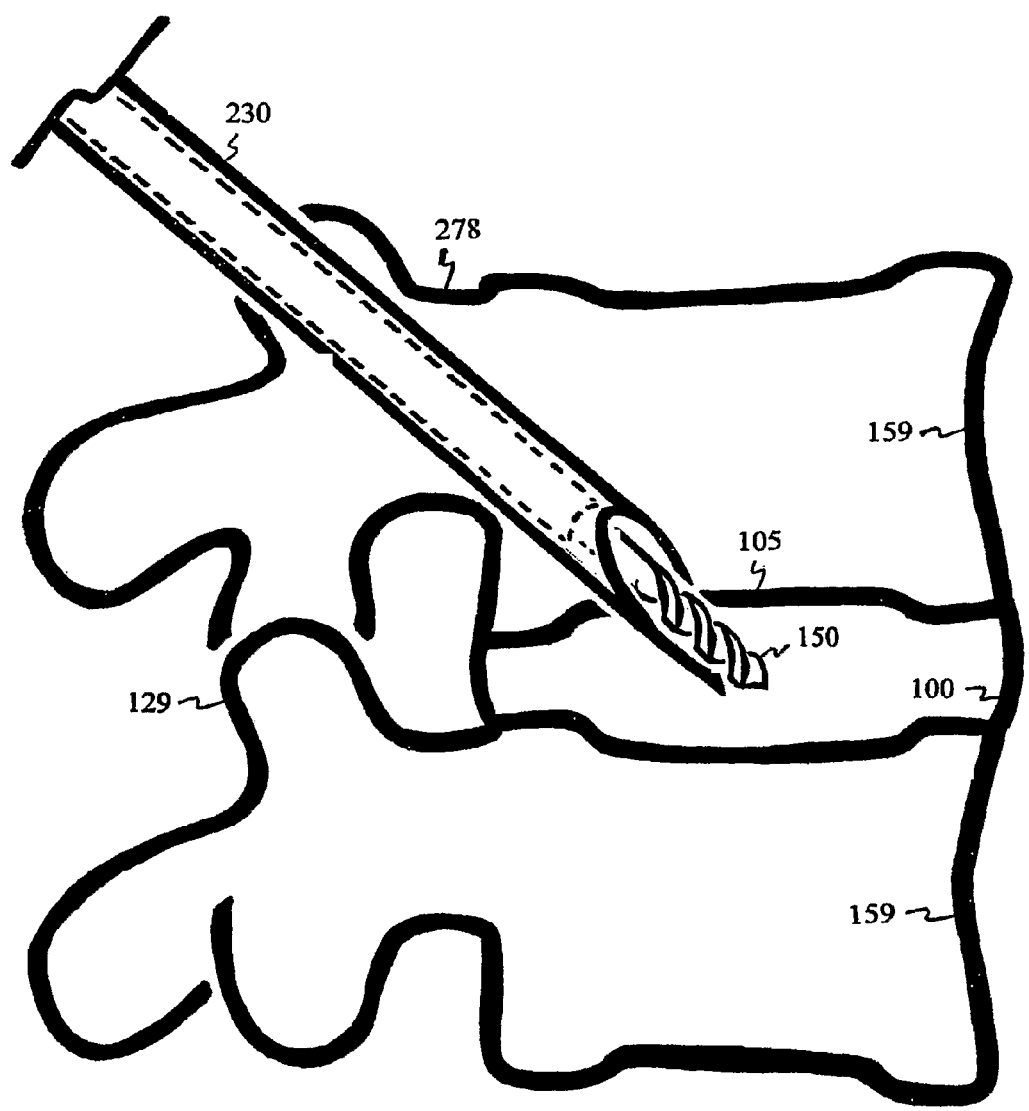
FIG. 19 shows advancement of the sleeve needle 230 sliding over the drill bit 150 into the drilled hole of the calcified endplate 105.

The sleeve needle 230 is held stationary, while the trocar 103 is withdrawn and replaced with a drill bit 150, drilling through the vertebral body 159 and calcified endplate 105, as shown in FIG. 18. The drill bit 150 contains a step or stop 279 to prevent excessive drilling through both endplates 105 of the disc 100. The drill bit 150 can also be coated with radiopaque, echogenic, MRI coating or other coating for image enhancement. The sleeve needle 230 is then advanced to slide over the drill bit 150 into the drilled hole of the calcified endplate 105, as shown in FIG. 19.

Figure 20:
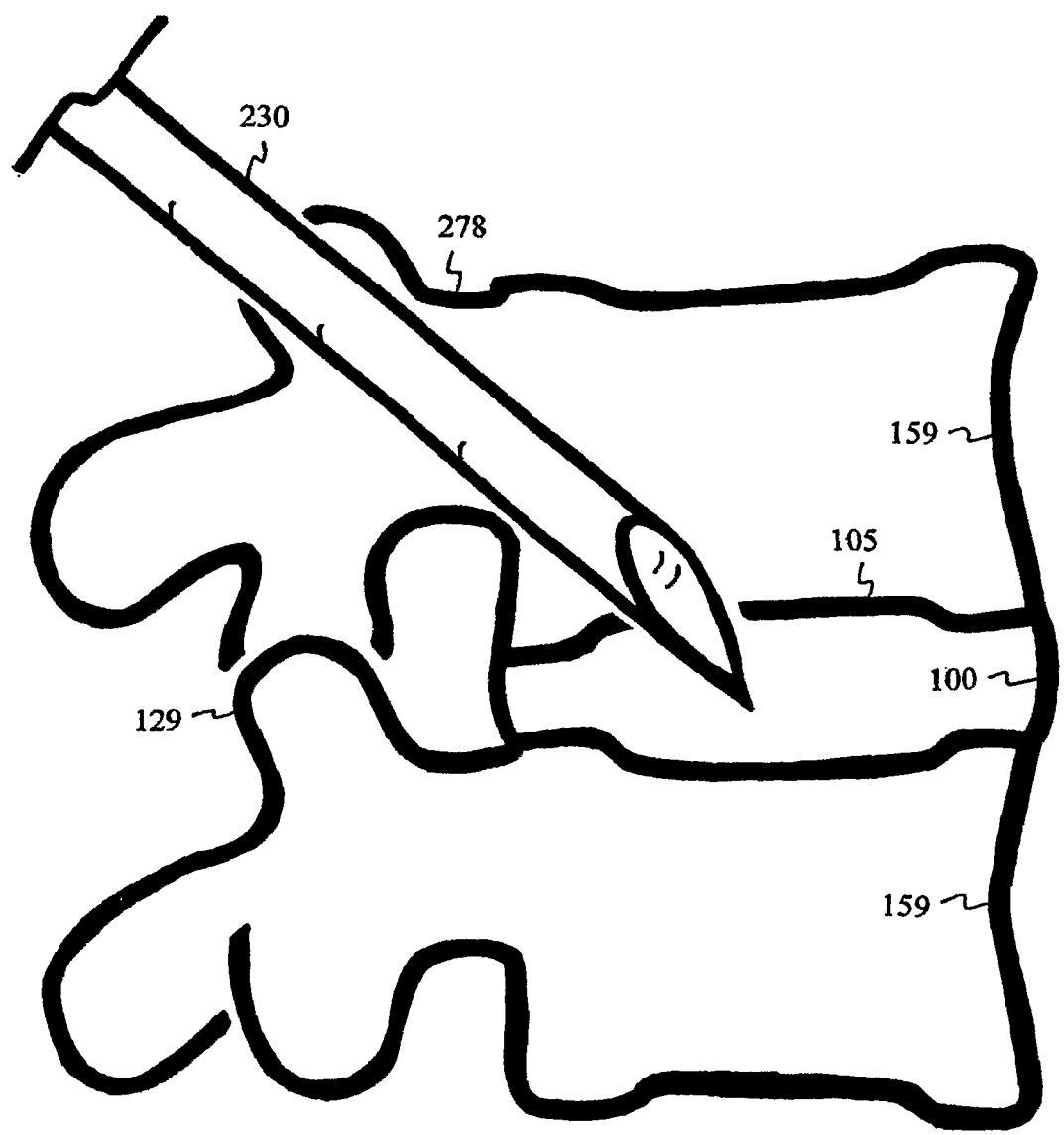
FIG. 20 shows withdrawal of the drill 150, leaving the tip of the sleeve needle 230 within the drilled hole of the calcified endplate 105.
Figure 21:
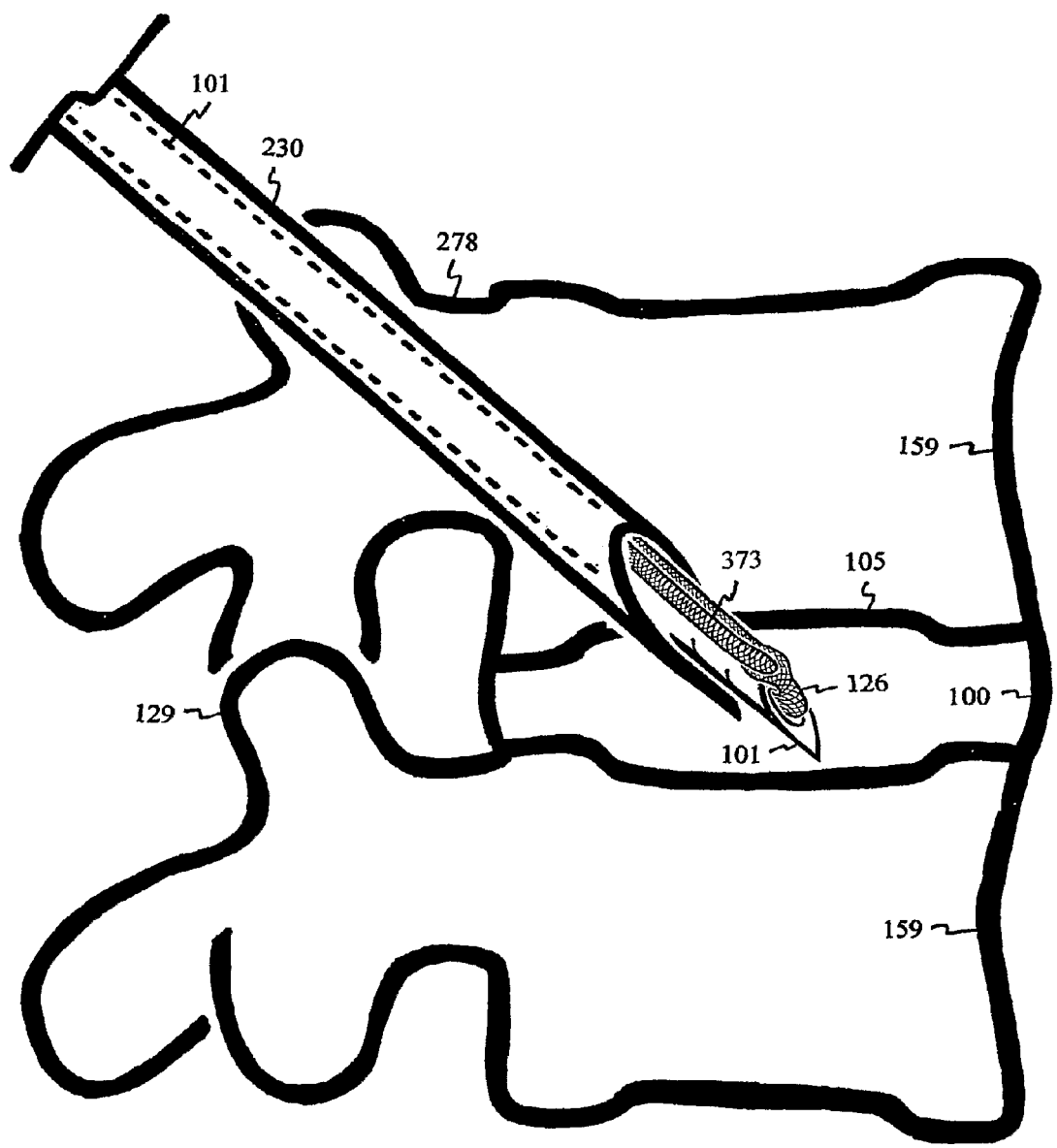
FIG. 21 shows endplate 105 puncture through the sleeve needle 230 by a needle 101 to press-fit the linked shunts 126, 373 into the disc 100.
Figure 22:
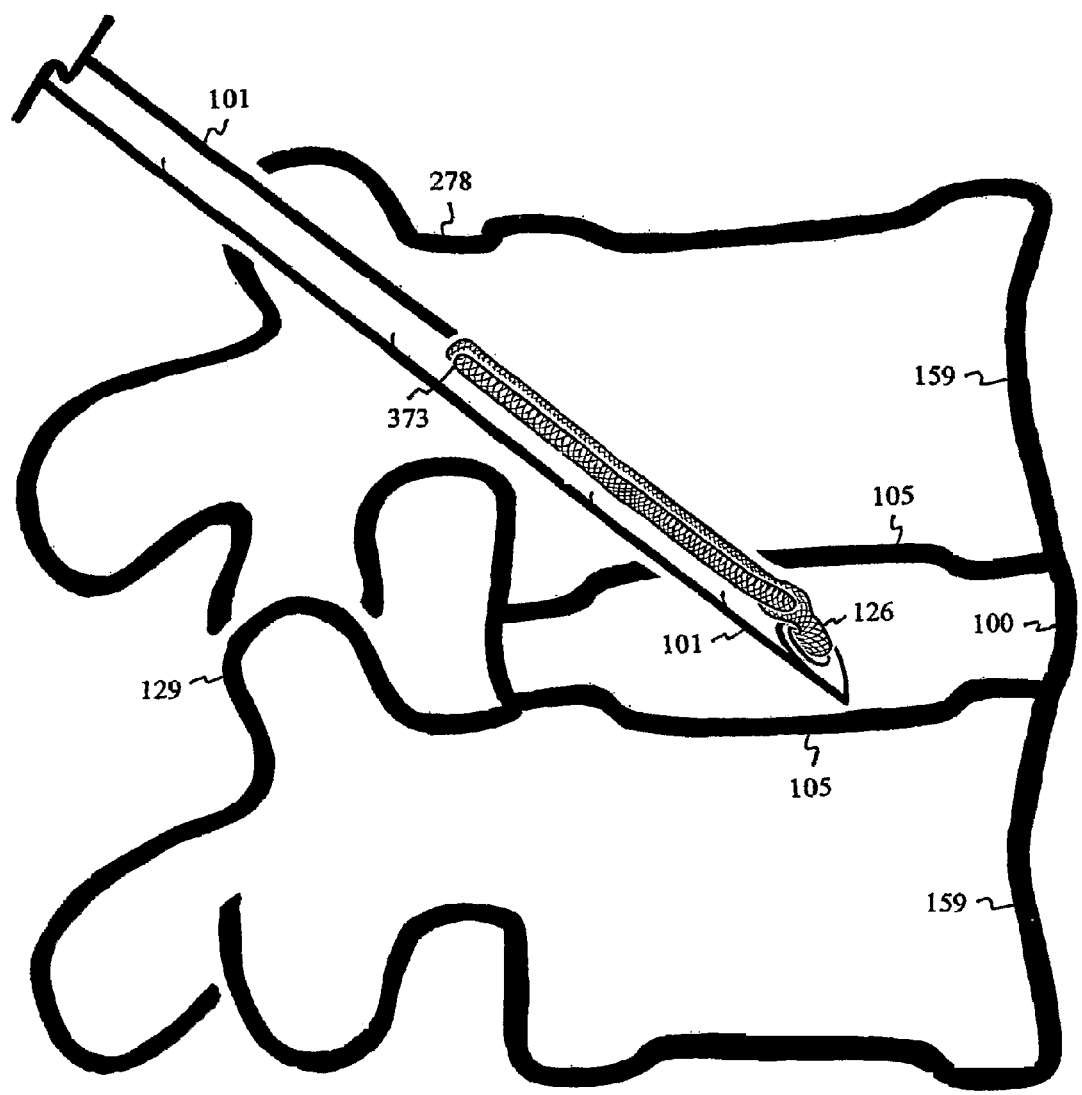
FIG. 22 shows withdrawal of the sleeve needle 230 to allow tissue contact with the linked shunts 126, 373 for friction assisted shunt deployment.
Figure 23:
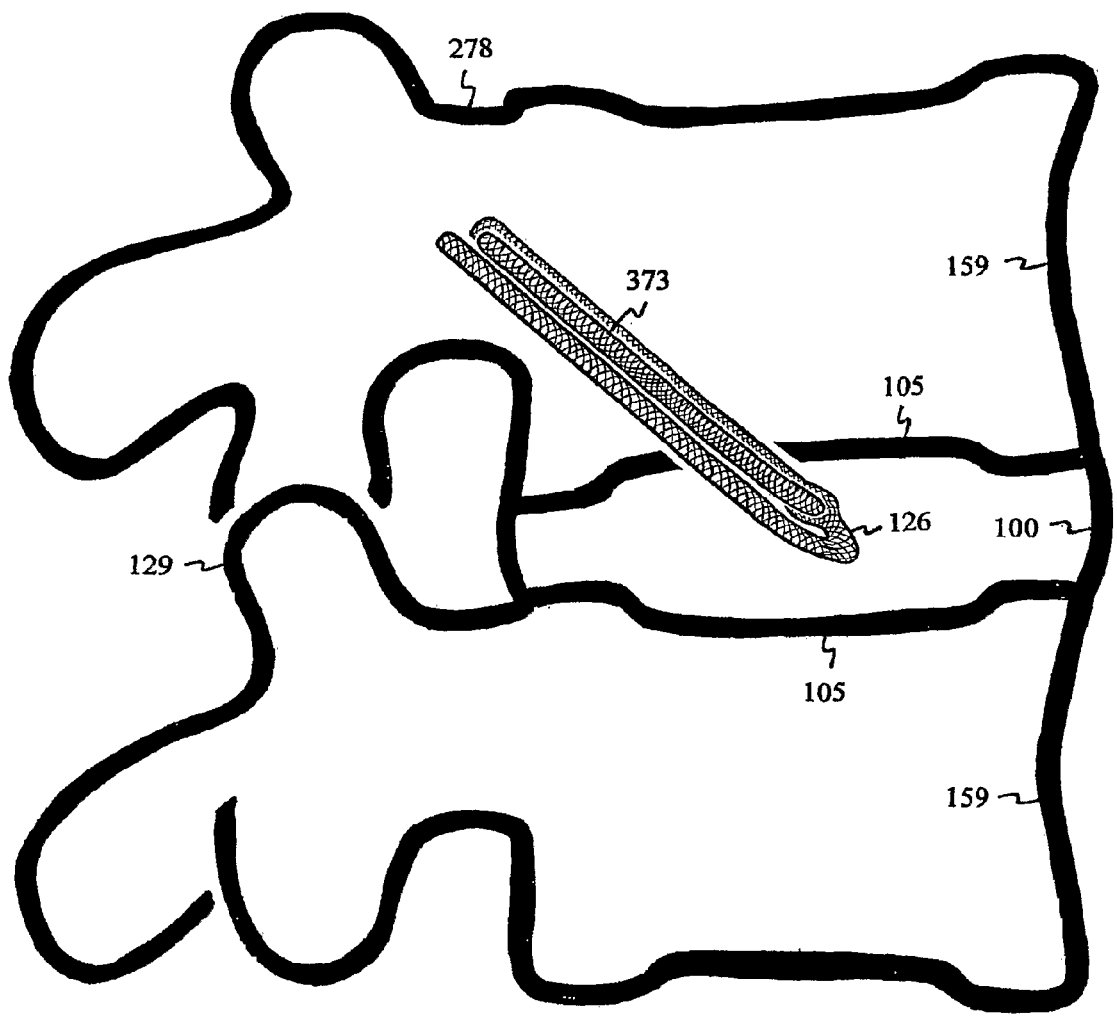
FIG. 23 shows deployment of the linked shunts 126, 373 by withdrawing the needle 101 to connect the avascular disc 100 with the interior of the vertebral body 159 to re-establish nutrients and waste exchange.

The drill bit 150 is withdrawn from the sleeve needle 230, leaving the tip of the sleeve needle 230 within the drilled hole of the calcified endplate 105, as shown in FIG. 20. The needle 101 of the linked shunts 126, 373 is inserted through the sleeve needle 230, puncturing and enlarging the drilled hole of the calcified endplate 105 and press-fitting into the degenerative disc 100, as shown in FIG. 21. Both the needle 101 and linked shunts 126, 373 can be coated with radiopaque, echogenic, MRI coating or other coating for image enhancement. FIG. 22 shows withdrawal of the sleeve needle 230 to allow tissue contact with the linked shunts 126, 373 for friction assisted shunt deployment. FIG. 23 shows deployment of the linked shunts 126, 373 by withdrawing the needle 101, thus connecting the avascular disc 100 to the interior circulation of the vertebral body 159 and re-establishing the exchange of nutrients, oxygen and waste.

Figure 24:
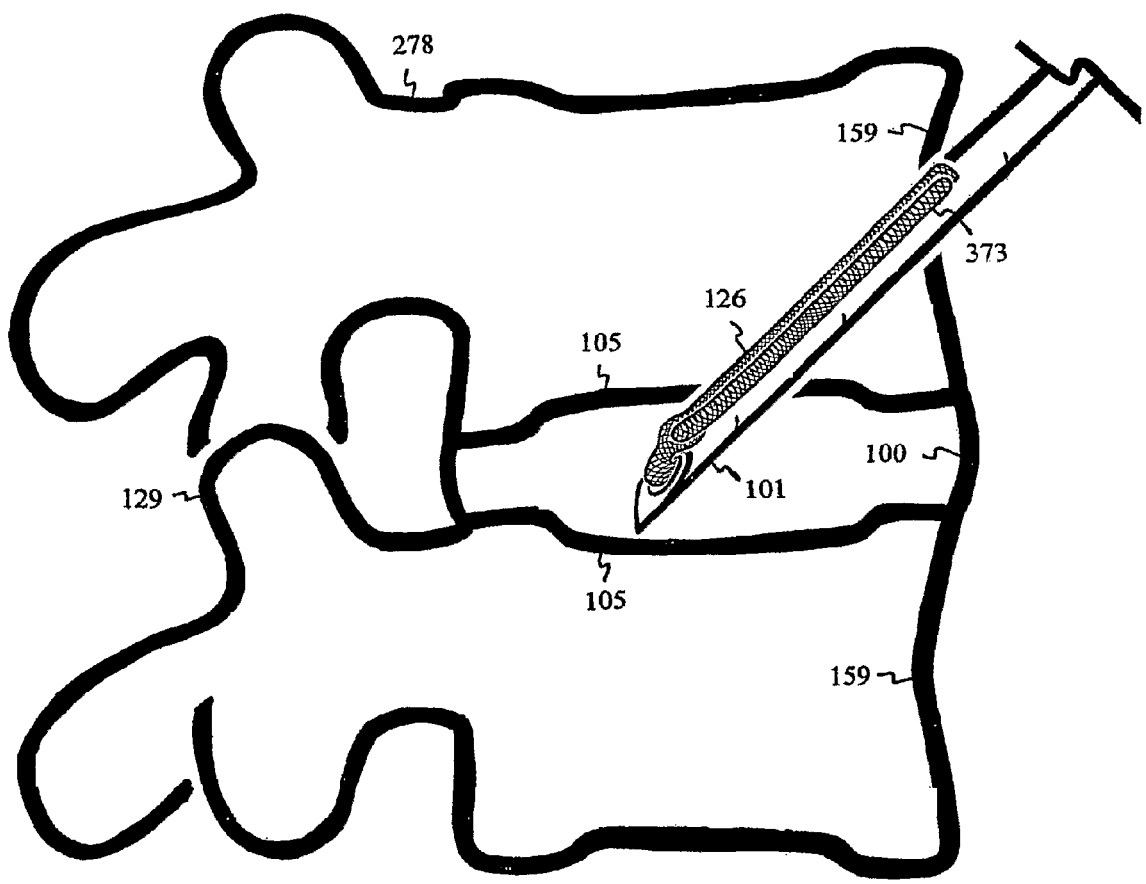
FIG. 24 shows an anterior approach using similar drilling procedure to puncture and deploy the linked shunts 126, 373 connecting the avascular disc 100 and the vertebral body 159.

Recurrent back pain is common among post-surgical patients. The pain often comes from progressive disc degeneration adjacent to the surgical levels. During surgeries for anterior spinal fusion or disc replacement, degeneration of the adjacent disc 100 can be minimized or halted by implanting disc shunts 126, 373 through the endplate 105. FIG. 24 shows an anterior approach using a drilling procedure similar to the pedicle approach. The linked shunts 126, 373 are implanted through the vertebral body 159 into the avascular disc 100 adjacent to the surgical level. Since the patient is already undergoing an open surgery, implantation of disc shunts 126, 373 through the endplate 105 or through the annulus is straight forward, low risk and cost effective to minimize recurrent pain or future surgery. Similarly, laminectomy or other posterior open surgical approaches also provide easy access for implanting annular or endplate shunts 126 into multiple degenerative discs 100.

The vertebral body 159 and endplate 105 of the patient may be soft enough for trocar 103 puncture. The trocar 103 can be tapped or lightly hammered through the vertebral body 159 and endplate 105 into the disc 100. The sleeve needle 230 is then inserted over the trocar 103, advanced into the endplate 105 and the disc 100. The trocar 103 is replaced by the U-shaped shunts 126, 373 and needle 101, as shown in FIG. 21.

Figure 25:
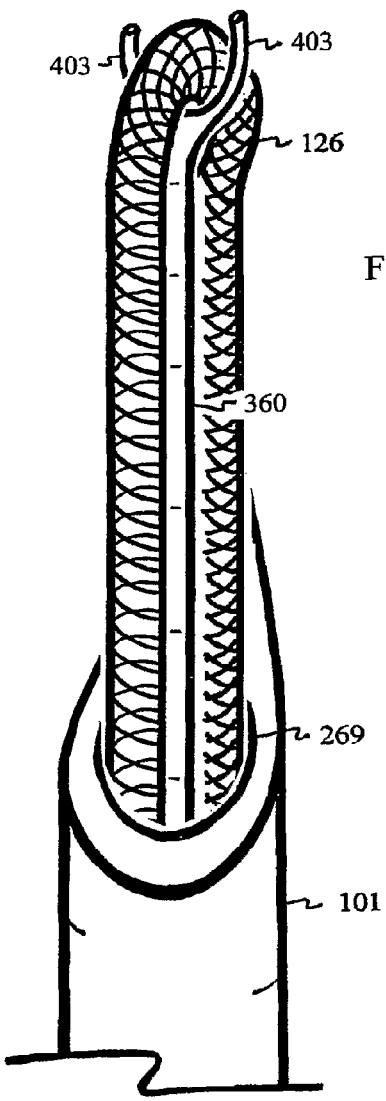
FIG. 25 shows a U-shaped shunt 126 supported between prongs 403 extended from a stem 360.
Figure 26:
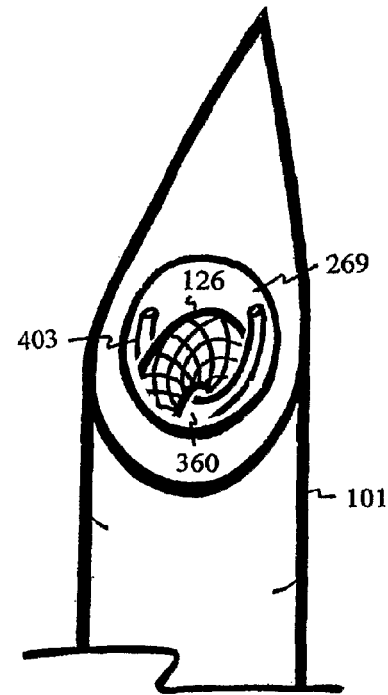
FIG. 26 shows the lumen 269 of a needle 101 housing the U-shaped shunt 126, prongs 403 and stem 360, for puncturing and delivering the shunt 126 into a disc 100.
Figure 27:
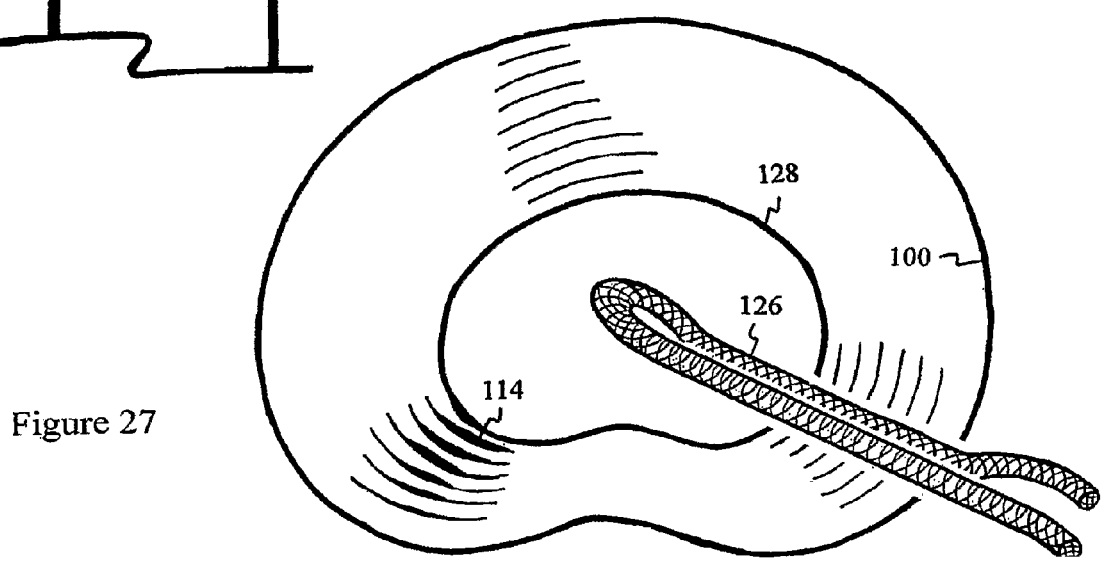
FIG. 27 shows a U-shaped shunt 126 delivered by disc 100 puncturing and withdrawing the needle 101 shown in FIG. 26, while holding the stem 360 stationary.

The U-shaped shunt 126 can also be delivered completely within the lumen 269 of a needle 101. FIG. 25 shows a U-shaped shunt 126 supported between prongs 403 extending from a stem 360. The U-shaped shunt 126, prongs 403 and stem 360 are housed within the lumen 269 of a needle 101, as shown in FIG. 26, capable of puncturing an intervertebral disc 100. After disc 100 puncturing, the needle 101 is withdrawn while holding the stem 360 stationary to deploy the U-shaped shunt 126 within the disc 100, as shown in FIG. 27. Distal portions or sections of the first end and second end of the U-shaped shunt 126 are adjacent or connected to the U-, V- or middle portion. The distal portions or sections of the first and second ends are in contact with each other after deployment the U-shaped shunt 126. Similar contact between the distal portions or sections of the first end and second end of the U-shaped shunt 126 are shown in FIGS. 15 and 23. Annular delamination 114 from decreased swelling disc pressure is also shown in FIG. 27.

Figure 28:
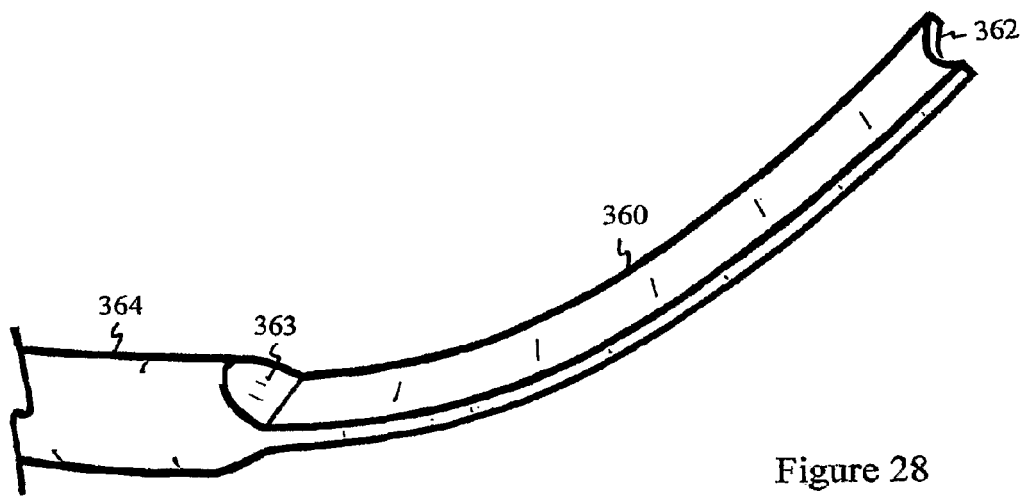
FIG. 28 shows an indentation 362 at the distal end of the stem 360 to support the U-portion of the shunt 126.
Figure 29:
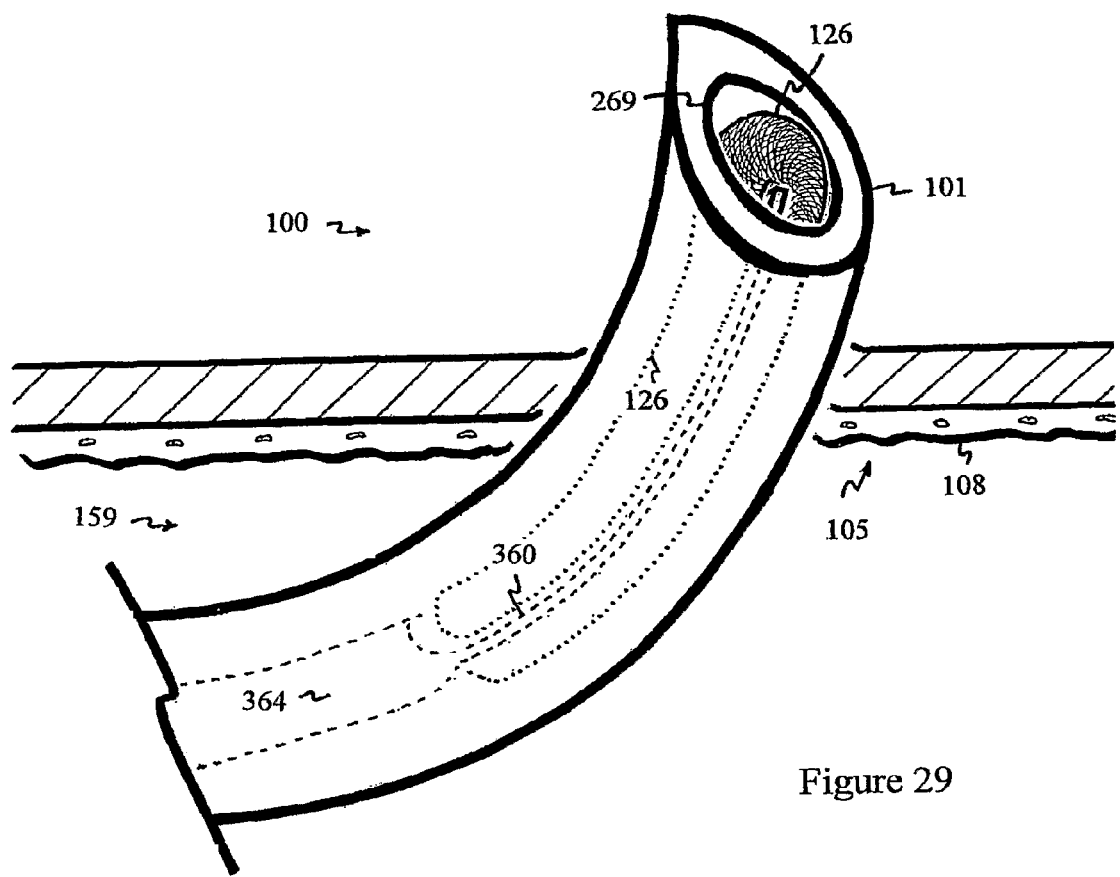
FIG. 29 shows a U-shaped shunt 126 supported by the flexible stem 360 within the lumen 269 of an elastically curved needle 101 puncturing through the calcified endplate 105.

FIG. 28 shows an indentation 362 for supporting the U-loop of the shunt 126. The ribbon-like stem 360 is thin to minimize space within the lumen 269 of the needle 101. The body 364 is thickened beyond the bevels 363 to strengthen the stem 363. FIG. 29 shows a U-shaped shunt 126 supported by a flexible stem 360 housed within the lumen 269 of an elastically curved needle 101 puncturing through a calcified layer 108 and cartilaginous endplate 105. The disc shunt 126 is deployed across the calcified endplate 105 from the vertebral body 159 into the disc 100 by withdrawing the needle 101 while holding the stem 360 stationary.

Figure 30:
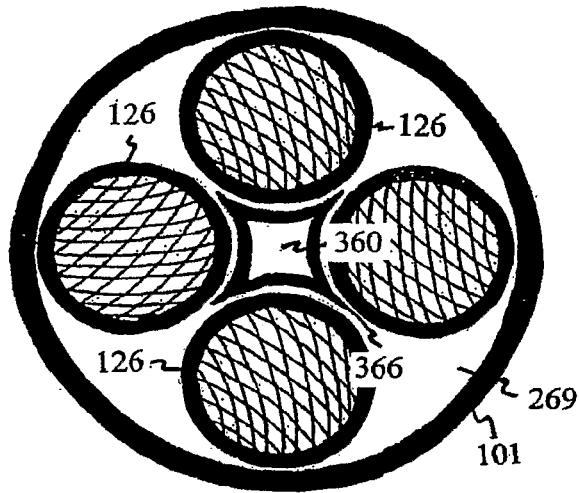
FIG. 30 shows a cross section of two U-shaped shunts 126 supported by a square-like stem 360 within the lumen 269 of a needle 101.
Figure 31:
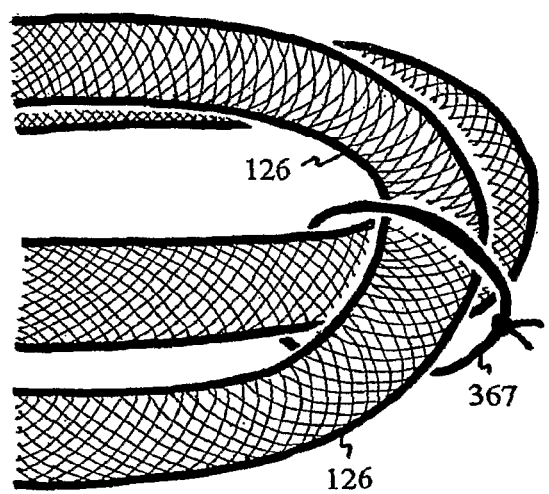
FIG. 31 shows a restriction device 367 holding the two U-shaped shunts together within a needle 101.

Multiple U-shaped shunts 126 can be delivered from the lumen 269 of the needle 101 and supported by a shape conforming stem 360, as shown in FIG. 30. The stem 360 can have longitudinal edges 366 to align the shunts 126 and prevent intertwining or tangling within the lumen 269. The distal ends or the U-loops of the multiple shunts 126 can have a restriction device 367, as shown in FIG. 31, to keep the U-shaped shunts 126 from unraveling and jamming within the lumen 269 of the needle 101. Similarly, multiple U-shaped shunts 126 can also be housed both inside and outside of the lumen 269 of the needle 101 to press-fit multiple U-shaped shunts 126 into a degenerative disc 100.

It is generally accepted that disc 100 degeneration is largely related to nutritional and oxygen deficiency. Especially in the supine position, disc pressure is low. During sleep, fluid from circulatory containing nutrients and oxygen is drawn through the shunt 126, 373 by (1) capillary action, (2) water absorbency of the shunt, (3) imbibing pull of the water-absorbing sulfated glycosaminoglycans within the disc 100, and/or (4) low pressure within the disc 100.

As a result, nutrients are drawn into the disc 100 through the semi-permeable shunt 126, 373 to biosynthesize the water retaining sulfated glycosaminoglycans and increase the swelling pressure within the disc 100. Restoration of swelling pressure in the nucleus pulposus 128 reinstates the tensile stresses within the collagen fibers of the annulus, thus reducing the inner bulging and shear stresses between annular layers. Similar to a re-inflated tire, disc 100 bulging is reduced and nerve impingement is minimized. The load on the facet joints 129 and segmental instability are reduced to minimize strain, wear and pain. Disc 100 height may also increase to reverse spinal stenosis.

Furthermore, adenosine triphosphate, ATP, is the high-energy compound essential for driving or energizing biochemical reactions, including the biosynthesis of the water retaining proteoglycans for sustaining compressive loads on the disc 100. Under anaerobic conditions, metabolism of each glucose molecule produces only two ATP and two lactic acids, which irritate the adjacent nerves. When oxygen permeates through the U-shaped shunt 126 and/or link shunt 373, thirty-six ATP are produced from each glucose molecule through glycolysis, citric acid cycle and electron transport chain under aerobic conditions to energize disc 100 regeneration and alleviate back pain.

In daily activities, such as walking, lifting and bending, pressure within the disc 100 greatly increases. The direction of the flow within the disc shunt 126, 373 is likely to reverse and flow from high pressure within the disc 100 to low pressure within vertebral bodies 159 or external fluid surrounding the disc 100. The lactic acid and carbon dioxide dissolved in the fluid within the nucleus pulposus 128 will slowly expel through the shunt 126 into bodily circulation. As a result, the lactic acid concentration will decrease, and pH within the disc 100 will normalize to reduce or alleviate pain from acid irritation.

Sodium carbonate, sodium bicarbonate, potassium carbonate, potassium bicarbonate, magnesium carbonate, calcium carbonate, barium carbonate, potassium phosphate, sodium phosphate or other buffering agent can be loaded in or coated on the shunt 126, 373 to neutralize lactic acid and spontaneously alleviate pain caused by acid irritation.

Similarly, magnesium oxide, magnesium hydroxide, sodium hydroxide, potassium hydroxide, barium hydroxide, cesium hydroxide, strontium hydroxide, calcium hydroxide, lithium hydroxide, rubidium hydroxide, neutral amines or other alkaline agent can be loaded in or coated on the shunt 126, 373 to neutralize lactic acid and spontaneously alleviate pain caused by acid irritation.

In addition, an initial supply of nutrients, such as sulfate, glucose, glucuronic acid, galactose, galactosamine, glucosamine, hydroxylysine, hydroxylproline, serine, threonine, chondroitin sulfate, keratan sulfate, hyaluronate, magnesium trisilicate, magnesium mesotrisilicate, magnesium oxide, Magnosil, Pentimin, Trisomin, orthosilicic acid, magnesium trisilicate pentahydrate, serpentine mineral, sodium metasilicate, silanolates, silanol group, sialic acid, silicic acid, boron, boric acid, minerals and/or other amino acids can be used to coat or load the shunts 126, 373 as additives to enhance or initiate the production of sulfated glycosaminoglycans and collagen within the degenerative disc 100. Growth factor, antibiotic, analgesic may also be helpful to load into or coat on the shunts 126, 373.

Hydrostatic pressure within the shunted disc 100 can be further preserved by a swellable and semi-permeable coating over the U-shaped shunts 126, 373 to seal the gap between the shunt 126, 373 and annulus or between the shunt 126, 373 and endplate 105. The swellable coating can be polyethylene glycol, crosslinked polyethylene glycol, polyurethane, swellable or elastic materials.

Fibrous formation over the shunts 126, 373 may affect the exchange of nutrients and waste between the disc 100 and bodily circulation. Immuno inhibitor can be coated or incorporated into the shunts 126, 373 to minimize fibrous formation or tissue response. Examples of immuno inhibitors include but are not limited to: actinomycin-D, aminopterin, azathioprine, chlorambucil, corticosteroids, crosslinked polyethylene glycol, cyclophosphamide, cyclosporin A, 6-mercaptopurine, methylprednisolone, methotrexate, niridazole, oxisuran, paclitaxel, polyethylene glycol, prednisolone, prednisone, procarbazine, prostaglandin, prostaglandin $E_1$, sirolimus, steroids, other immune suppressant drugs or other immune suppressant coatings.

The U-shaped shunts 126, 373 can be loaded or coated with a calcium channel blocker to minimize calcification, mineralization or blockade of the shunts 126, 373. The calcium channel blocker can also disperse from the shunt 126, 373 to prevent formation of or even open calcified layers of the cartilaginous endplate 105, to enhance diffusion of nutrients and waste between the disc 100 and bodily circulation. The calcium channel blocker can be one of the dihydropyridines, phenylalkylamines, benzothiazepines or others. The calcium channel blocker for loading into the shunt 126, 373 can be Amlodipine, Felodipine, Isradipine, Lacidipine, Lercanidipine, Nicardipine, Nifedipine, Nimodipine, Nisoldipine, Verapamil, Diltiazem or other calcium channel blocker.

The U-shaped shunts 126, 373 can be loaded or coated with a chelating agent to minimize calcification, mineralization or blockade of the shunts 126, 373. The chelating agent can also disperse from the shunt 126, 373 to extract calcium ion, opening calcified layers of the cartilaginous endplate 105 to enhance diffusion of nutrients and waste between the disc 100 and bodily circulation. The chelating agent can be ethylene diamine tetra acetate, diethylene triamine penta acetate, meso-2,3-dimercapto succinic acid, desferoxamine, 2,3-dimercapto-1-propane sulfonate, D-penicillamine, defarasirox, dimercaprol, N,N-bis(carboxymethyl)glycine, morpholine dithiocarbamate, tetra ammonium ethylene diamine diacetic acid dithiocarbamate, ammonium diethanolamine dithiocarbamate, sodium diethyl dithio carbamate, N-benzyl-D-glucamine dithio carbamate, alpha lipoic acid, tartaric acid, glutathione, methionine and/or L-arginine. In general, the coating of chelating agent of the shunts 126, 373 can contain a carboxylated group, amine group or thiol group. Sodium or potassium carboxylate is preferred to minimize acidic irritation during extraction of calcium ion from the calcified endplate 105.

The U-shaped shunts 126, 373 may have pore sizes ranging from 301 micrometer to 1 nanometer. The U-shaped shunts 126, 373 may also have a length-wise gradient of various pore sizes to limit permeability. The pore sizes of the permeable gradient of the shunts 126, 373 can range from 301 micrometer, 100 micrometer, 50 micrometer, 10 micrometer, 1 micrometer, 700 nanometer, 500 nanometer, 300 nanometer, 100 nanometer, 50 nanometer, 30 nanometer, 10 nanometer, 5 nanometer to 1 nanometer to prevent infiltration of IgA, IgD, IgE, IgG, IgM, cytokines or other initiators triggering an immune reaction.

In addition, the U-shaped shunts 126, 373 may have sections containing different pore sizes to create regions of size exclusion or permeabilities along the shunts 126, 373. The pore sizes of the shunts 126, 373 may decrease toward the section near the nucleus pulposus 128 to minimize immune responses to the nucleus pulposus 128 without excluding large nutrients from coming into or metabolites from going out of the middle portion of the annulus. Hence, the shunts 126, 373 can have permeable regions ranging from 200000, 100000, 70000, 50000, 30000, 10000, 5000, 3000, 1000, 700, 400 to 200 gram per mole of solutes.

Healthy intervertebral discs 100 are avascular and immuno-isolated. To ensure avascular and immuno-isolated conditions, the shunts 126, 373 can be incorporated, coated or partially coated with an anti-angiogenic compound. Examples of anti-angiogenic compounds include, but are not limited to, Marimastat from British Biotech [a synthetic inhibitor of matrix metalloproteinases (MMPs)], Bay 12-9566 from Bayer (a synthetic inhibitor of tumor growth), AG3340 from Agouron (a synthetic MMP inhibitor), CGS 27023A from Novartis (a synthetic MMP inhibitor), COL-3 from Collagenex (a synthetic MMP inhibitor. Tetracycline® derivative), Neovastat from Aeterna, Sainte-Foy (a naturally occurring MMP inhibitor), BMS-275291 from Bristol-Myers Squib (a synthetic MMP inhibitor), TNP-470 from TAP Pharmaceuticals, (a synthetic analogue of fumagillin; inhibits endothelial cell growth), Thalidomide from Celgene (targets VEGF, bFGF), Squalamine from Magainin Pharmaceuticals (Extract from dogfish shark liver; inhibits sodium-hydrogen exchanger, NHE3), Combretastatin A-4 (CA4P) from Oxigene, (induction of apoptosis in proliferating endothelial cells), Endostatin collagen XVII fragment from EntreMed (an inhibition of en dothelial cells), Anti-VEGF Antibody from Genentech, [Monoclonal antibody to vascular endothelial growth factor (VEGF)], SU5416 from Sugen (blocks VEGF receptor signaling), SU6668 from Sugen (blocks VEGF, FGF, and EGF receptor signaling), PTK787/ZK 22584 from Novartis (blocks VEGF receptor signaling), Interferon-alpha (inhibition of bFGF and VEGF production), Interferon-alpha (inhibition of bFGF and VEGF production), EMD121974 from Merck, KcgaA (small molecule blocker of integrin present on endothelial cell surface), CAI from NCI (inhibitor of calcium influx), Interleukin-12 from Genetics Institute (Up-regulation of interferon gamma and IP-10), IM862 from Cytran, Avastin, Celebrex, Erbitux, Herceptin, Iressa, Taxol, Velcade, TNP470, CM101, Carboxyamidotriazole, Anti-neoplastic urinary protein, Isotretionin, Interferon-alpha, Tamoxifen, Tecogalan combrestatin, Squalamine, Cyclophosphamide, Angiostatin, Platelet factor-4, Anginex, Eponemycin, Epoxomicin, Epoxy-β-aminoketone, Antiangiogenic antithrombin III, Canstatin, Cartilage-derived inhibitor, CD59 complement fragment, Fibronectin fragment, Gro-beta, Heparinases, heparin hexasaccharide fragment, Human chorinonic gonadotropin, Interferon (alpha, beta or gamma), Interferon inducible protein (IP-10), Interleukin-12 (IL-12), Kringle 5 (plasminogen fragment), Tissue inhibitors of metalloproteinases, 2-Methoxyestradiol Panzem), Placental ribonuclease inhibitor, Plasminogen activator inhibitor, Prolactin 16 kD fragment, Retinoids, Tetrahydrocortisol-S, Thrombospondin-1, Transforming growth factor beta, Vasculostatin, and Vasostatin (calreticulin fragment).

A wide range of non-degradable materials can be used to fabricate the U-shaped shunt 126 and link shunt 373. Biocompatible polymers, such as Nylon, polytetrafluoroethylene, polypropylene, polyethylene, polyamide, polyester, polyurethane, silicon, poly-ether-ether-ketone, acetal resin, polysulfone, polycarbonate, silk, cotton, or linen are possible candidates. Fiberglass can also be a part of the shunt 126, 373 to provide capillarity for transporting nutrients and waste.

Part of the shunt 126, 373 can include one of the following materials, but is not limited to carboxymethyl cellulose, cellulose acetate, cellulose sulfate, cellulose triacetate, chitin, chitosan, chloroprene, ethylenevinyl acetate, fluoro-silicon hydrogel, hyaluronan, hyaluronate, neoprene, polyacrylamide, polyacrylate, polyamide, polyacrylonitrile, poly-butylene terephthalate, poly-dimethyl-siloxane, poly-hydroxy-ethyl-acrylate, poly-hydroxy-ethyl-methacrylate, polyhydroxy-methyl methacrylate, polymethacrylate, polymethylmethacrylate, polypropylene oxide, poly-siloxane, polyvinyl alcohol, poly-vinylpyrrolidone, silanol and vinyl methyl ether.

For investigative purposes, a biodegradable shunt 126, 373 may show efficacy within weeks or months. Since the shunt 126, 373 degrades within months, any unforeseen adverse outcome would be nullified or negated. If the investigative-degradable shunt 126, 373 shows efficacy, a permanent or non-degradable shunt 126, 373 can then be installed to provide continuous treatment or benefits. The biodegradable shunt 126, 373 can be made with polylactate, polyglycolic, poly-lactide-co-glycolide, polycaprolactone, trimethylene carbonate, silk, catgut, collagen, poly-p-dioxanone or combinations of these materials. Other degradable polymers, such as polydioxanone, polyanhydride, trimethylene carbonate, poly-beta-hydroxybutyrate, polyhydroxyvalerate, poly-gama-ethyl-glutamate, poly-DTH-iminocarbonate, poly-bisphenol-A-iminocarbonate, poly-ortho-ester, polycyanoacrylate or polyphosphazene can also be used.

The shunt 126, 373 can be a suture with a proven safety record. The shunt 126, 373 can be formed by molding, extruding, braiding, weaving, coiling, spiraling or machining. The shunt 126, 373 can also be called or classified as a conduit, wick, tube, braided suture, braided filaments, thread or sponge. The disc 100 installed with the shunt 126, 373 can be called the shunted disc 100.

The needle 101, trocar 103, sleeve needle 230 and stem 360 can be made with stainless steel, titanium, nickel-titanium or other alloy. The needle 101, trocar 103, sleeve needle 230, stem 360 or shunt 126, 373 can be coated with lubricant, analgesic, antibiotic, radiopaque, echogenic or MRI visible agent.

Disc cells can be drawn from another disc 100 within the patient to inject with a syringe into the shunted disc 100 to expedite disc regeneration. Gene therapy can also be done in the shunted disc 100 to promote disc regeneration.

Since cellularity within discs 100 is always low, the shunted disc 100 can be further revitalized by injection of donor cells from an external source to expedite regeneration. The avascular disc 100 is well sealed. Even small ions, such as sulfate, and small molecules, such as proline, are greatly limited from diffusing into the nucleus pulposus 128. The well-sealed disc 100 may be able to encapsulate donor cells from a disc 100 of a human cadaver without triggering an immune response. For disc 100 regeneration, the donor cells can also be stem cells, notochord or chondrocytes from tissue cultures, animals or biotechnology. Cells sensitive to sterilization can be loaded aseptically. The method for injecting donor cells into a shunted disc 100 can be done in multiple stages, separated by days, weeks, months or even years. Initial shunt 126, 373 deployment prepares the biological conditions, including pH, electrolytic balance and nutrients, to favor cell proliferation before cell injection. Donor cells can also be encapsulated within biodegradable capsules, seeded within the shunt 126, 373 and released after suitable biological conditions have been attained or achieved by the U-shaped shunt 126, 373.

In recent years, cell transplants from cadavers or live donors have been successful in providing therapeutic benefits. For example, islet cells from a donor pancreas are injected into a type I diabetic patient's portal vein leading into the liver. The islets begin to function as they normally do in the pancreas by producing insulin to regulate blood sugar. However, to keep the donor cells alive, the diabetic patient requires a lifetime supply of anti-rejection medication, such as cyclosporin A. In addition to the cost of anti-rejection medication, the long-term side effects of these immuno-suppressive drugs include cancer. The benefit of cell transplant may not out weigh the potential side effects.

The shunted disc 100 with the semi-permeable shunt 126, 373 can be used as a semi-permeable capsule to encapsulate therapeutic donor cells. The shunted disc 100 maintains immuno-isolation for the donor cells to evade immuno-response of the patient. In addition, nutrients and oxygen essential for the donor cells are supplied through the U-shaped shunts 126, 373. Hence, the need for immuno-suppressive medication is avoided. A variety of donor cells can be harvested and/or cultured from the pituitary gland (anterior, intermediate or posterior lobe), hypothalamus, adrenal gland, adrenal medulla, fat cells, thyroid, parathyroid, pancreas, testes, ovary, pineal gland, adrenal cortex, liver, renal cortex, kidney, thalamus, parathyroid gland, ovary, corpus luteum, placenta, small intestine, skin cells, stem cells, gene therapy, tissue engineering, cell culture, other glands or tissues. The donor cells can be from humans, animals or cell cultures. In supine sleeping position, nutrients and oxygen are supplied through the shunt 126, 373 to the donor cells. During waking hours while the pressure within the disc 100 is high, products biosynthesized by these cells are expelled through the shunt 126, 373 into the vertebral bodies 159 or outer annulus, then into the veins, bodily circulation and target sites, when and where the demands are high during waking hours.

The product biosynthesized by the donor cells within the shunted disc 100 can be adrenaline, adrenocorticotropic hormone, aldosterone, androgens, angiotensinogen (angiotensin I and II), antidiuretic hormone, atrial-natriuretic peptide, calcitonin, calciferol, cholecalciferol, calcitriol, cholecystokinin, corticotropin-releasing hormone, cortisol, dehydroepiandrosterone, dopamine, endorphin, enkephalin, ergocalciferol, erythropoietin, follicle stimulating hormone, γ-aminobutyrate, gastrin, ghrelin, glucagon, glucocorticoids, gonadotropin-releasing hormone, growth hormone-releasing hormone, human chorionic gonadotrophin, human growth hormone, insulin, insulin-like growth factor, leptin, lipotropin, luteinizing hormone, melanocyte-stimulating hormone, melatonin, mineralocorticoids, neuropeptide Y, neurotransmitter, noradrenaline, oestrogens, oxytocin, parathyroid hormone, peptide, pregnenolone, progesterone, prolactin, pro-opiomelanocortin, PYY-336, renin, secretin, somatostatin, testosterone, thrombopoietin, thyroid-stimulating hormone, thyrotropin-releasing hormone, thyroxine, triiodothyronine, trophic hormone, serotonin, vasopressin, or other therapeutic products.

The products (hormones, peptides, neurotransmitter, enzymes, catalysis or substrates) generated within the shunted disc 100 may be able to regulate body functions including blood pressure, energy, neuro-activity, metabolism, activation and suppression of gland activities. Some hormones and enzymes govern, influence or control eating habits and utilization of fat or carbohydrates. These hormones or enzymes may provide weight loss or gain benefits. Producing neurotransmitters, such as dopamine, adrenaline, noradrenaline, serotonin or γ-aminobutyrate from the donor cells within the shunted disc 100 can treat depression, Parkinson's disease, learning disability, memory loss, attention deficit, behavior problems, metal or neuro-related disease.

Release of the products biosynthesized by the donor cells within the shunted disc 100 is synchronized with body activity. During activities of daily living, the pressure within the shunted disc 100 is mostly high to expel the products biosynthesized by the donor cells into circulation to meet the demands of the body. In the supine position, the flow within the shunt 126, 373 reverses, bringing nutrients and oxygen into the disc 100 to nourish the cells. Using islets of Langerhans from the donor's pancreas as an example, production of insulin will be induced in the shunted disc 100 during sleeping hours when glucose enters into the disc 100. During waking hours when disc pressure is high, insulin will be expelled through the shunt 126, 373 into circulation to draw sugars into cell membranes for energy production. At night, the insulin released from the shunted disc 100 will be minimal to prevent hypoglycemia. In essence, products biosynthesized by the donor cells will be released concurrent with physical activity to meet the demands of the body.

Some biosynthesized products from the donor cells are appropriately deposited through the vertebral body 159, then into bodily circulation. Other products may be more effectively transported through the outer annulus and diffused through the abdomen into bodily circulation. Some other products may be far more effective by entering into the muscles connected to the U-shaped disc shunt 126, 373.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments.

It should be clear to one skilled in the art that the current chemicals, biochemicals, drugs, methods, embodiments, materials, constructions, cells, tissues or incision sites are not the only uses for which the invention may be used. Different chemicals, constructions, methods, coating or designs for the modified U-shaped disc shunt 126, 373 can be substituted and used. Nothing in the preceding description should be taken to limit the scope of the present invention. The full scope of the invention is to be determined by the appended claims.

What is claimed is:

1. A device for treatment of an intervertebral disc, the device comprising:
    a needle comprising a distal end, proximal end, an outside wall and a longitudinal lumen extending in from said distal end thereof,
    a first shunt comprising a first end, a second end and a middle portion, wherein at least a portion of said first end is located in said longitudinal lumen, and wherein said first shunt is lumenless,
    wherein said first shunt comprises pore sizes ranging from 301 micrometer to 1 nanometer,
    wherein said middle portion, when entering into the intervertebral disc, is distal to said first and second ends,
    wherein said first end comprises a distal portion adjacent to said middle portion,
    wherein said second end comprises a distal section adjacent to said middle portion,
    and wherein said distal portion of said first end contacts said distal section of said second end, when said first shunt is deployed in the intervertebral disc.
2. The device of claim 1, wherein said second end is located outside said longitudinal lumen, when entering into the intervertebral disc.
3. The device of claim 1, wherein said distal end comprises an inner wall, wherein at least a portion of said inner wall is blunt or rounded.
4. The device of claim 3, wherein prior to deployment, a portion of said first shunt rests against said blunt or rounded portion of said inner wall.
5. The device of claim 1, wherein at least a portion of said distal end is sharpened and beveled.
6. The device of claim 1, further comprising a slit in said needle, said slit extending from said distal end.
7. The device of claim 6, wherein prior to deployment, a portion of said first shunt is located within said slit.
8. The device of claim 1, further comprising a protrusion extending from said first shunt.
9. The device of claim 1, wherein said needle has a round cross section.
10. The device of claim 1, wherein said needle has a non-round cross section.
11. The device of claim 1, further comprising a stem located at least partially within said longitudinal lumen, and wherein said stem comprises a distal edge.
12. The device of claim 11, wherein said distal edge comprises an indentation.
13. The device of claim 11, wherein said stem comprises an insertion position and a deployment position, wherein in said insertion position, said stem is located within said longitudinal lumen, and wherein in said deployment position at least a portion of said distal edge extends distally from said distal end of said needle.
14. The device of claim 11, wherein prior to deployment, said stem engages said first shunt.
15. The device of claim 11, wherein said stem has a flat ribbon shape.
16. The device of claim 11, wherein the stem is flexible.
17. The device of claim 1, further comprising a second shunt linking to said first shunt.
18. The device of claim 17, wherein said second shunt passes through a portion of said first shunt.
19. The device of claim 17, wherein said second shunt is attached to said first shunt.
20. The device of claim 17, wherein said second shunt comprises pore sizes ranging from 301 micrometer to 1 nanometer.
21. The device of claim 17, wherein at least one of said first and second shunts is formed with sections having different pore sizes.
22. The device of claim 21, wherein said different pore sizes range from 301 micrometer to 1 nanometer.
23. The device of claim 17, wherein at least one of said first and second shunts further comprises a buffer coating.
24. The device of claim 23, wherein said buffer coating is chosen from the group consisting of sodium carbonate, sodium bicarbonate, potassium carbonate, potassium bicarbonate, magnesium carbonate, calcium carbonate, barium carbonate, potassium phosphate and sodium phosphate.
25. The device of claim 17, wherein at least one of said first and second shunts further comprises an alkaline coating.
26. The device of claim 25, wherein said alkaline coating is chosen from the group consisting of magnesium oxide, magnesium hydroxide, sodium hydroxide, potassium hydroxide, barium hydroxide, cesium hydroxide, strontium hydroxide, calcium hydroxide, lithium hydroxide, rubidium hydroxide and neutral amines.
27. The device of claim 17, wherein at least one of said first and second shunts further comprises an additive coating.
28. The device of claim 27, wherein said additive coating is chosen from the group consisting of sulfate, glucose, glucuronic acid, galactose, galactosamine, glucosamine, hydroxylysine, hydroxylproline, serine, threonine, chondroitin sulfate, keratan sulfate, hyaluronate, magnesium trisilicate, magnesium mesotrisilicate, magnesium oxide, Magnosil, Pentimin, Trisomin, orthosilicic acid, magnesium trisilicate pentahydrate, serpentine material, sodium metasilicate, silanolates, silanol group, sialic acid, silicic acid, boron, boric acid, minerals and other amino acids, growth factor, antibiotic and analgesic.

29. The device of claim 17, wherein at least one of said first and second shunts further comprises an immuno inhibitor coating.

30. The device of claim 29, wherein said immuno inhibitor coating is chosen from the group consisting of actinomycin-D, aminopterin, azathioprine, chlorambucil, corticosteroids, crosslinked polyethylene glycol, cyclophosphamide, cyclosporin A, 6-mercaptopurine, methylprednisolone, methotrexate, niridazole, oxisuran, paclitaxel, polyethylene glycol, prednisolone, prednisone, procarbazine, prostaglandin, prostaglandin $E_1$, sirolimus and steroids.

31. The device of claim 17, wherein at least one of said first and second shunts further comprises a calcium channel blocker coating.

32. The device of claim 31, wherein said calcium channel blocker coating is chosen from the group consisting of Amlodipine, Felodipine, Isradipine, Lacidipine, Lercanidipine, Nicardipine, Nifedipine, Nimodipine, Nisoldipine, Verapamil and Diltiazem.

33. The device of claim 17, wherein at least one of said first and second shunts further comprises a chelating agent coating.

34. The device of claim 33, wherein said chelating agent coating is chosen from the group consisting of ethylene diamine tetra acetate, diethylene triamine penta acetate, meso-2,3-dimercapto succinic acid, desferoxamine, 2,3-dimercapto-1-propane sulfonate, D-penicillamine, defarasirox, dimercaprol, N,N-bis(carboxymethyl) glycine, morpholine dithiocarbamate, tetra ammonium ethylene diamine diacetic acid dithiocarbamate, ammonium diethanolamine dithiocarbamate, sodium diethyl dithio carbamate, N-benzyl-D-glucamine dithio carbamate, alpha lipoic acid, tartaric acid, glutathione, methionine, L-arginine, carboxylated group, amine group and thiol group.

35. The device of claim 17, wherein at least one of said first and second shunts is configured to transport oxygen.

36. The device of claim 17, wherein at least one of said first end, second end and second shunt extends into a muscle.

37. The device of claim 17, wherein at least one of said first end, second end and second shunt extends into a vertebral body.

38. A method for implanting a shunt to treat an intervertebral disc, the method comprising the steps of:
penetrating into an intervertebral disc with a needle and a shunt, wherein said shunt comprises pore sizes ranging from 301 micrometer to 1 nanometer, a mid portion, a first end and a second end, wherein at least one of said first and second ends is located in a longitudinal lumen of said needle, and wherein said mid portion is distal to said first and second ends;
withdrawing said needle from the intervertebral disc, and leaving said mid portion located within the intervertebral disc and at least one of said first end and second end outside the intervertebral disc and in bodily circulation, thereby exchanging nutrients, oxygen and lactic acid between the intervertebral disc and bodily circulation through said shunt.

39. The method of claim 38, further comprising the step of:
puncturing through an endplate with said needle and said shunt, and wherein the bodily circulation is in a vertebral body.

40. The method of claim 38, further comprising the step of:
puncturing through a muscle with said needle and said shunt, wherein the bodily circulation is in the muscle.

41. The method of claim 38, wherein said shunt is configured to transport oxygen.

* * * * *